(12) United States Patent
Bushweller et al.

(10) Patent No.: US 9,926,290 B2
(45) Date of Patent: Mar. 27, 2018

(54) INHIBITORS OF INV(16) LEUKEMIA

(71) Applicant: University of Virginia Patent Foundation, Charlottesville, VA (US)

(72) Inventors: John H. Bushweller, Crozet, VA (US); Jolanta Grembecka, Ann Arbor, MI (US); Anuradha Illendula, Crozet, VA (US); Lauren Mishra, Tucson, AZ (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/967,568

(22) Filed: Dec. 14, 2015

(65) Prior Publication Data

US 2016/0096820 A1 Apr. 7, 2016

Related U.S. Application Data

(63) Continuation of application No. 14/271,978, filed on May 7, 2014, now Pat. No. 9,221,764, which is a continuation of application No. 13/320,123, filed as application No. PCT/US2010/034748 on May 13, 2010, now Pat. No. 8,748,618.

(60) Provisional application No. 61/177,730, filed on May 13, 2009.

(51) Int. Cl.
*C07D 401/04* (2006.01)
*C07D 401/14* (2006.01)
*C07D 405/04* (2006.01)
*C07D 235/18* (2006.01)

(52) U.S. Cl.
CPC ......... *C07D 401/04* (2013.01); *C07D 235/18* (2013.01); *C07D 401/14* (2013.01); *C07D 405/04* (2013.01)

(58) Field of Classification Search
CPC .................................................... C07D 401/04
USPC ...................................................... 546/273.4
See application file for complete search history.

(56) References Cited

U.S. PATENT DOCUMENTS 4,192,880 A * 3/1980 Tsukamoto .......... C07D 235/18
514/338

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burgers Medicinal Chemistry and Drug Discovery. 5th ed. vol. 1: Principles and Practice. pp. 949-982, 1995.*
Bundgaard, Design of Prodrugs, Chapter 1, p. 1, 1985.*
Silverman, Prodrugs and Drug Delivery Systems, the Organic Chemistry of Drug Design and Drug action, Chapter 8, pp. 352-400, 1992.*
Hulikal, Deuterium Labeled Compounds in Drug Discovery Process, Abstract, 2010.*
Pimlott, PubMed Abstract (Nucl Med Commun. 26(3):183-8), 2005.*
Banker et al., Prodrugs, Modern Pharmaceutics, 3rd edition, Revised and Expanded, pp. 451 and 596.*
Jordan "Tamoxifen . . . " Nature Rev. v.2, p. 205-213 (2003).*
Hisano et al., "Synthesis o Benzoxazoles, etc.," Chem. Pharm. Bull. 30(8) 2996-3004 (1982).i.*
Chakravarti et al., "A Quantitative, etc.," Indian J. Oharm. Sci., 1999, 61(4) 206-212.*

* cited by examiner

*Primary Examiner* — Patricia L Morris
(74) *Attorney, Agent, or Firm* — Rodney L. Sparks

(57) ABSTRACT

This invention describes the development of targeted small molecule inhibitors of the inv(16) fusion, the causative agent in ~12% of acute myeloid leukemia (AML). The inv(16) fusion results in expression of the CBFβ-SMMHC fusion protein in the blood cells of afflicted patients. The present invention provides compounds which inhibit the function of both CBFβ and the CBFβ-SMMHC fusion. These compounds block the growth of an inv(16) leukemia cell line as well as increase its apoptosis, while showing minimal effects against non inv(16) cell lines. As a mechanism to develop inhibitors with selectivity for the CBFβ-SMMHC fusion protein, the present invention further provides dimeric derivatives of these compounds which show both increased potency as well as selectivity for CBFβ-SMMHC. These compounds show potent inhibition of an inv(16) leukemia cell line with minimal effects on non inv(16) cell lines. Analysis of the pharmacokinetics of the developed compounds has made it possible to improve the lifetime of the compound in the plasma of mice to a level commensurate with long-term treatment.

3 Claims, 12 Drawing Sheets

1. Ethyleneglycol di(p-toluenesulfonate), K₂CO₃, DMF, 80°C
2. n-BuLi, DMF, -78°C to RT, THF
3. Nitroaniline, Na₂S₂O₄, EtOH, 70°C where R, R₁ and n =

1. R = -OCH₃, R₁ = H, n = 0
2. R = -OCH₃, R₁ = H, n = 1
3. R = -OCH₃, R₁ = H, n = 3
4. R = -OCH₂CH₃, R₁ = H, n = 0
5. R = -SCH₃, R₁ = H, n = 0
6. R = -OCF₃, R₁ = H, n = 0
7. R = -F, R₁ = H, n = 0
8. R = R₁ = -Cl, n = 0
9. R = -N(CH₃)₂, R₁ = H, n = 0
10. R =   R₁ = H, n = 0

INHIBITORS OF INV(16) LEUKEMIA

CROSS REFERENCE TO RELATED APPLICATIONS

This application is a continuation application of U.S. patent application Ser. No. 14/271,978, filed May 7, 2014, which is a continuation application of U.S. application Ser. No. 13/320,123, filed Nov. 11, 2011, now U.S. Pat. No. 8,748,618, granted on Jun. 10, 2014, which is a national stage filing of International Application No. PCT/US2010/034748, filed May 13, 2010, which claims priority under 35 U.S.C. § 119(e) to U.S. Provisional Application Ser. No. 61/177,730 filed May 13, 2009, the disclosures of which are incorporated by reference in their entirety herein.

This invention was made with government support under Grant No. CA140398 awarded by the National Institutes of Health. The government has certain rights in the invention.

BACKGROUND

Core Binding Factor.

Core binding factors (CBFs) are heterodimeric transcription factors consisting of a DNA-binding CBFα subunit (Runx1, Runx2, or Runx3) and a non-DNA-binding CBFβ subunit. Homozygous disruption of Runx1 or Cbfb in mice results in mid-gestation embryonic lethality and a profound block in definitive hematopoiesis (Okuda, van Deursen et al. 1996; Sasaki, Yagi et al. 1996; Wang, Stacy et al. 1996; Wang, Stacy et al. 1996), establishing these two proteins as essential for proper hematopoiesis. The embryos lack definitive hematopoietic progenitors, enucleated erythrocytes, and mature myeloid lineage cells because of the failure of hematopoietic stem cells to emerge from the endosteum at day E10.5. Runx1 deficient embryos lack any transplantable hematopoietic stem cell (HSC) activity, the lineage from which all differentiated lineages develop with the exception of erythrocytes, establishing CBF as a critical regulator of hematopoietic stem cell function (Cai, de Bruijn et al. 2000).

Studies in mice of dosage effects of Runx1 and Cbfb on hematopoiesis show significant effects with even modest changes in the level of either protein. Two-fold changes in Runx1 dosage affect timing of hematopoietic stem cell emergence in the embryo and the numbers of committed progenitors in the embryo and adult (Cai, de Bruijn et al. 2000; North, de Bruijn et al. 2002; Lacaud, Kouskoff et al. 2004). These studies suggest that the dosage of Runx1 affects the balance between hematopoietic stem cells and committed progenitors in the embryo. Consistent with this, alteration of RUNX dosage in humans is associated with disease. The familial platelet disorder with a propensity to develop AML (FPD/AML) syndrome is an inherited disease displaying altered hematopoiesis (thrombocytopenia and impaired platelet function) and a high risk of developing acute myeloid leukemia (AML) (Ho, Otterud et al. 1996; Song, Sullivan et al. 1999). These patients have loss-of-function mutations in RUNX1. In addition, 3-5% of sporadic leukemias display loss-of-function mutations in RUNX1 (Osato, Yanagida et al. 2001).

Alteration of Cbfb dosage also shows significant defects in hematopoietic compartments. A recent study showed that a 3-fold reduction in Cbfb dosage resulted in a reduction in the number mature thymocytes (T cells) and a 6-fold reduction resulted in no thymocytes (Talebian, Li et al. 2007). It is clear that the dosages of both Runx1 or Cbfb are critical for normal hematopoiesis and regulation of HSCs.

Structural and Functional Characterization of CBF.

The structure of the heterodimerization domain of CBFβ was first determined using NMR spectroscopy by our lab (Huang, Peng et al. 1999) and others (Goger, Gupta et al. 1999). The CBFβ heterodimerization domain has a novel α/β fold composed of a central six-stranded highly-twisted β-sheet surrounded by four α-helices and one $3_{10}$ helix. NMR chemical shift perturbation analysis was used to map the binding site for the Runx1 Runt domain on CBFα (Huang, Peng et al. 1999). Based on this data, we carried out extensive Ala mutagenesis on CBFβ to identify the energetic hotspots for binding (Tang, Shi et al. 2000). Subsequent crystal structures of ternary complexes (see below) confirmed the importance of this region for interaction with Runx1.

We and others also determined the structure of the DNA and CBFβ binding domain of Runx1, termed the Runt domain, using NMR (Berardi, Sun et al. 1999; Nagata, Gupta et al. 1999). Structural studies of the Runt domain were carried out using Runt domain-DNA complexes because of the poor behavior of the isolated proteins in solution (Berardi, Sun et al. 1999; Nagata, Gupta et al. 1999; Perez-Alvarado, Munnerlyn et al. 2000). The Runt domain is a β-sandwich protein with no α-helical content, as was predicted from an earlier circular dichroism (CD) study (Crute, Lewis et al. 1996). The fold identified for the Runt domain belongs to the classic immunoglobulin (Ig) fold, specifically the s-type Ig fold best exemplified by the structure of the fibronectin repeat element. Interestingly, this fold has been identified in the DNA binding domains of a number of other critical mammalian transcription factors including NF-κB, NFAT, p53, STAT-1, and the T-domain. Thus, the Runt domain belongs to a family of structurally-related s-type Ig fold DNA-binding domains. For all of these structurally-related proteins, binding to DNA is mediated by the loop regions that connect the various β-strands. As was done for CBFβ, we carried out a chemical shift perturbation mapping study to identify the CBFα binding site on the Runt domain (Tang, Crute et al. 2000). Based on this data, we carried out extensive Ala mutagenesis to identify the energetic hotspots for CBFβ binding on the Runt domain (Zhang, Li et al. 2003). We also carried out an extensive Ala mutagenesis study to identify the energetic hotspots for DNA binding (Li, Yan et al. 2003).

Crystal structures of ternary complexes containing CBFβ, the Runt domain, and DNA have been determined using X-ray crystallography (Bravo, Li et al. 2001; Tahirov, Inoue-Bungo et al. 2001). These structures have provided a wealth of detailed information on the interaction between the Runt domain and DNA as well as between the Runt domain and CBFβ. As seen in all the other Ig-fold DNA-binding proteins mentioned above, the Runt domain makes contacts in both the major and minor grooves of the DNA using loops extending from one end of the barrel. These structures also clearly show the location and positioning of the CBFβ subunit. As predicted based on biochemical experiments, CBFβ does not make any direct contacts to the DNA, but modulates the Runt domain's binding affinity indirectly, i.e. allosterically.

Crystal structures of the Runx1 Runt domain alone have also been determined (Backstrom, Wolf-Watz et al. 2002; Bartfeld, Shimon et al. 2002). A previous NMR study of the isolated Runt domain alone was able to characterize the β-barrel, but limited solubility and extensive exchange broadening for resonances of the residues in the DNA-binding loops limited the structural characterization (Perez-Alvarado, Munnerlyn et al. 2000). With the addition of a high-resolution structure of the isolated Runt domain, detailed structural information is available for this domain alone, in complex with CBFβ or DNA, and in a ternary complex with both CBFβ and DNA. This makes possible comparisons among the structures to identify structural changes in the Runt domain that occur upon binding. Both CBFβ and DNA induce very similar changes in the structure of the Runt domain (Backstrom, Wolf-Watz et al. 2002; Bartfeld, Shimon et al. 2002), arguing for the concept that the CBFβ subunit does indeed stabilize the DNA-binding conformation of the Runt domain. Indeed, we have shown by NMR relaxation studies that CBFβ alters an existing conformational equilibrium in the Runt domain which explains how this allosteric regulation is achieved (Yan, Liu et al. 2004).

Inv(16) Leukemia.

Two of the four genes encoding CBF subunits are proto-oncogenes commonly activated in human leukemias. The RUNX1 subunit is encoded by the acute myeloid leukemia 1 (AML1) or RUNX1 gene which is disrupted by a variety of chromosomal translocations (Look 1997), all of which are associated with myeloid and lymphocytic leukemias. The gene encoding CBFβ (CBFB) is disrupted by the pericentric inversion of chromosome 16 [inv(16)(p13q22)], and less frequently by the t(16;16)(p13q22), associated with 100% of AML-M4Eo subtype (Liu, Tarle et al. 1993), resulting in a fusion protein containing most of the CBFβ protein (N-terminal 165 amino acids) fused to the coiled-coil tail region of smooth muscle myosin heavy chain (SMMHC) (see FIG. 1). The inv(16) is associated with ~12% of de novo acute myeloid leukemias in humans (Look 1997). The CBFβ-SMMHC fusion protein acts as a dominant repressor of CBF function (Liu, Tarle et al. 1993), binding RUNX1 and dysregulating the expression of multiple genes required for normal hematopoiesis.

Mice heterozygous for a knocked-in Cbfb-MYH11 allele displayed a very similar phenotype to that seen for the complete knockout of Runx1 or CBFβ, namely lethality at embryonic day 12 accompanied by hemorrhaging and a severe block in definitive hematopoiesis (Castilla, Wijmenga et al. 1996). Heterozygous embryos expressing one copy of CBFβ-SMMHC and one copy of CBFβ displayed a very similar phenotype to that seen for the complete knockout of Runx1 or CBFβ, namely lethality at day 12 with severe hemorrhages and a complete block in hematopoietic development. Further analysis showed that the presence of CBFβ-SMMHC specifically blocks maturation of lymphoid and myeloid lineages. These data clearly establish CBFβ-SMMHC as a dominant negative inhibitor of CBF function.

Previous studies have shown that CBFβ-SMMHC is necessary but not sufficient to cause leukemia in mouse models. In studies carried out by Dr. Lucio Castilla, chimeric mice generated from Cbfb$^{Cbfb-MYH11/+}$ embryonic stem cells were shown to be highly predisposed to the development of AML upon treatment with chemical (ENU) or retroviral mutagenesis (Castilla, Garrett et al. 1999) (Castilla, Perrat et al. 2004). The observed morphology of these mice closely mimics that seen for patients with AMLM4Eo. A more recent study in Dr. Castilla's lab used a conditional Cbfb$^{Cbfb-MYH11/+}$ knock in mouse to demonstrate that activation of CBFβ-SMMHC expression in bone marrow induces accumulation of myeloid progenitors that transform to full blown leukemia in 3 to 5 months (Kuo, Landrette et al. 2006). All these studies clearly establish CBFβ-SMMHC as essential for inv(16) leukemogenesis and argue strongly that targeted inhibition of this fusion protein would have therapeutic value.

In patients with inv(16) leukemia, leukemic cells frequently present additional mutations that could synergize in leukemogenesis. The most common mutations are activating mutations in the receptor tyrosine kinases c-Kit and FLT3 (Reilly 2005). This agrees well with the (at least) "two-hit hypothesis" (Dash and Gilliland 2001; Gilliland and Tallman 2002) that postulates that leukemia requires a combination of a mutation that blocks differentiation and a second that enhances proliferation. Hits that block differentiation often involve transcription factors such as the creation of the CBFβ-SMMHC fusion protein, whereas those that enhance proliferation often involve mutations that create a ligand-independent activated receptor tyrosine kinase or the associated RAS pathway. In support of this view, a recent study showed cooperativity between inv(16) and the FLT3 activated form FLT3ITD (Kim, Klug Blood 2008). Interestingly, molecular analysis of human AML samples at diagnosis and relapse indicate that these secondary mutations are not always present at relapse, strongly suggesting that while inv(16) may occur in the HSCs, the FLT3-ITD mutation may arise in later progenitors.

Mechanism of CBFβ-SMMHC Mediated Leukemogenesis.

Expression of CBFβ-SMMHC in cultured cells results in altered cellular localization of Runx1. Normally, Runx1 shows nuclear localization, but when co-expressed with CBFβ-SMMHC, both Runx1 and CBFβ-SMMHC are found predominantly in the cytoplasm (Lu, Maruyama et al. 1995; Liu, Wijmenga et al. 1996; Adya, Stacy et al. 1998; Kanno, Kanno et al. 1998). These results form the basis for one of the proposed mechanisms of the dominant negative activity of CBFβ-SMMHC, namely that CBFβ-SMMHC sequesters Runx1 in the cytoplasm thereby preventing it from reaching the nucleus (reviewed in (Shigesada, van de Sluis et al. 2004)). The C-terminal tail of CBFβ-SMMHC which includes an assembly competence domain (ACD) has been shown by co-immunoprecipitation to bind to a number of proteins involved in transcriptional repression including mSIN3 and HDACs (Lutterbach, Hou et al. 1999; Durst, Lutterbach et al. 2003). Based on these results, a second model for the dominant negative activity of CBFβ-SMMHC has been proposed in which CBFβ-SMMHC acts at the level of the promoter as a transcriptional repressor by means of recruitment of specific co-repressors (reviewed in (Hiebert, Lutterbach et al. 2001)).

Importantly, neither Runx1$^{+/-}$ nor Cbfb$^{+/-}$ mice exhibit the dramatic hematopoietic defects associated with the CBFB-MYH11 knock-in allele (Castilla, Wijmenga et al. 1996; Okuda, van Deursen et al. 1996; Sasaki, Yagi et al. 1996; Wang, Stacy et al. 1996; Wang, Stacy et al. 1996). Neither of the two models mentioned above explained how more than half of the normal Runx1-CBFβ activity is lost. Our hypothesis was that CBFβ-SMMHC inactivated more than 50% of Runx1-CBFβ function because of its altered affinity for Runx1. Using isothermal titration calorimetry, we showed that CBFβ-SMMHC binds ~10-fold more tightly to the Runx1 Runt domain than does wildtype CBFβ (Lukasik, Zhang et al. 2002). NMR studies of a complex between a functional CBFβ-SMMHC domain and the Runt domain show that the Runt domain in this complex is contacting both the CBFβ portion of the protein and a specific region in the SMMHC domain. These results demonstrate that the increased affinity of CBFβ-SMMHC for Runx1 contributes to the disruption of normal hematopoiesis.

More recently, we have also shown that CBFβ-SMMHC inhibits the DNA binding of the Runt domain, providing yet another layer of inhibition of Runx activity. Consistent with this, previous studies have shown decreased RUNX binding to the MPO promoter (Cao, Britos-Bray et al. 1997) and to the INK4b promoter (Markus, Garin et al. 2007) in the presence of CBFβ-SMMHC. All of the functional studies clearly establish that the binding of CBFβ-SMMHC to the Runt domain of RUNX1 is essential for its function and therefore establish this as an appropriate target for inhibition.

Role of Inv(16) in Leukemia Stem Cell Properties.

Patients with inv(16) AML usually undergo aggressive chemotherapy regimes involving cytotoxic drugs such as Ara-C and anthramycin. This treatment is better tolerated by young patients showing a 5 year overall survival of 45% to 65% (Ravandi, Burnett et al. 2007; Pulsoni, Iacobelli et al. 2008). However, most patients are older and the 5 year overall survival for patients older than 60 years old is about 20% (Farag, Archer et al. 2006). These data clearly indicate targeted therapies that can improve the therapeutic response for inv(16) AML patients are essential.

Emerging literature suggests that inability to cure cancers with current therapies, including cytotoxic chemotherapy, kinase inhibitors, or monoclonal antibodies, may be attributed to a population of so-called cancer stem cells or cancer initiating cells that are resistant to treatment, are quiescent, have long term self-renewal potential, and can fully recapitulate tumor phenotype at time of relapse. Inv(16) AML is a good example of this failure because inv(16) patients invariably show, at time of relapse, the inv(16) rearrangement, although other mutations detected at diagnosis (RAS, FLT3ITD or KIT) may or may not be detected at relapse (Nakano, Kiyoi et al. 1999; Kottaridis, Gale et al. 2002; Shih, Liang et al. 2008).

Because of the critical role of CBFβ and RUNX1 in regulating hematopoietic stem cells, dysregulation of this pathway by CBFβ-SMMHC (or other CBF fusion proteins such as AML1-ETO or TEL-AML1), will lead to the aforementioned cancer stem cell properties such as long term self renewal potential. In addition, microarray analysis of CBF leukemias indicates alteration of the levels of proteins involved in DNA repair (Alcalay, Orleth et al. 2001; Xu, Li et al. 2007), leading to enhanced mutagenesis rates and a likely increase in the rate of acquisition of secondary mutations such as those found in c-Kit and FLT3 which have been shown to accelerate leukemogenesis. As relapse of inv(16) AML is invariably accompanied by increase of inv(16)+ positive cells, it is thought that relapse results from a failure of treatment to eradicate leukemia stem cells. In addition, the observation that a patient diagnosed with inv(16) AML later relapsed with an inv(16)+ pro-B cell leukemia, suggests that the inv(16) rearrangement had occurred in a stem cell/multipotent progenitor with reduced proliferation capacity (Boeckx, van der Velden et al. 2004).

Protein-Protein Interaction Inhibitors (PPIs).

Protein-protein interactions play a critical role in all aspects of signaling in the cell. In terms of their biological importance, these are highly attractive targets. However, until recently protein-protein interactions were widely considered to be undruggable, i.e., targets with a very low likelihood of success. This view was based on the large surface area and lack of curvature, i.e. pockets amenable to small molecule binding, frequently found at such protein interfaces. That view is rapidly changing as increasing numbers of such inhibitors are reported (Cochran 2000; Toogood 2002; Veselovsky, Ivanov et al. 2002; Gadek and Nicholas 2003; Fry 2006). Indeed, a recent review listed 17 targets for which such inhibitors have been developed (Gadek and Nicholas 2003).

Protein-protein interactions play a particularly important role in the regulation of transcription where the assembly of appropriate protein-protein complexes is essential for appropriate gene regulation. To that end, inhibition of protein-protein interactions involving transcription factors has substantial potential to alter gene expression and thereby the expression profile of cancerous cells (Arndt 2006). One recent success story in this regard is the development of inhibitors of the MDM2-p53 interaction. Binding of MDM2 to p53 leads to enhanced proteasome degradation of p53. Elevated levels of MDM2 are seen in a number of cancers. Roche initially developed a high potency inhibitor of this interaction (Vassilev, Vu et al. 2004) and others have developed additional inhibitors (Shangary, Qin et al. 2008). These inhibitors have been shown to abrogate the effects of reduced p53 dosage or mutant p53 by inhibiting this interaction thereby increasing the level of p53 in cells and enhancing p53 mediated apoptosis (Vassilev, Vu et al. 2004; Tovar, Rosinski et al. 2006; Efeyan, Ortega-Molina et al. 2007). These results demonstrate that targeting protein-protein interactions with small molecules is feasible and provide validation for our proposal to develop inhibitors of the CBFβ-SMMHC-RUNX interaction.

Targeted Therapy for Leukemia.

The general aim of targeted therapy against leukemia is to use our understanding of the cellular programs associated with the pathology of leukemia to design treatments with a markedly improved therapeutic index. The majority of such studies in the leukemia field have focused on targeting activated components of the cytokine receptor signaling pathway. One classic example in leukemia is the small molecule imatinib, which acts by targeting the ATP-pocket of the ABL kinase, thereby blocking the tyrosine kinase activity of BCR-ABL in chronic myelogenous leukemia (Druker 2004; Lydon and Druker 2004). The use of imatinib has improved CML treatment dramatically. Second generation inhibitors such as dasatinib are also efficacious against imatinib resistant CML. The application of this approach to other leukemias, however, has thus far been less fruitful. Clinical trials are now underway to test the therapeutic index of inhibitors for other components of cytokine receptor pathways compromised in leukemias, such as inhibitors of activated FLT3 receptor (CEP-701, MLN 518, and PKC 412) and JAK2 kinase, although it is unclear whether these inhibitors will show significant improvement in therapeutic index.

The identification of molecules that inhibit AML fusion oncogenes, thus abrogating the block in differentiation and inducing apoptosis, has thus far been lacking. Previous studies of targeted therapy reveal two aspects which are critical in the development of an effective drug: 1) the molecule should inhibit the oncogene function and induce cell differentiation or death with minimal alteration of normal hematopoietic progenitors and 2) the drug should effectively target the quiescent leukemia stem cells, not only the LSC-derived proliferating cells.

There is a long felt need in the art for compositions and methods useful for preventing and for treating acute myeloid leukemia, particularly involving the inv(16) fusion. The present invention satisfies these needs.

SUMMARY OF THE INVENTION

Any chance of eradicating the leukemia stem cell population and thereby achieving better long-term survival for leukemia patients must focus on inhibition of the activity of the specific oncogene driving the leukemia stem cell properties. The present invention provides synthetic schemes and compounds derived during the development of inhibitors targeting CBFβ-SMMHC as a more effective therapeutic approach to inv(16) leukemia. Because the interaction of CBFβ-SMMHC with the Runt domain of RUNX1 is essential for its activity, the focus of the present application is on developing inhibitors of this protein-protein interaction.

In one embodiment, a compound of the invention has the following general structure useful for inhibiting proliferation of inv(16) leukemia cells and for treating inv(16) leukemia:

Formula I

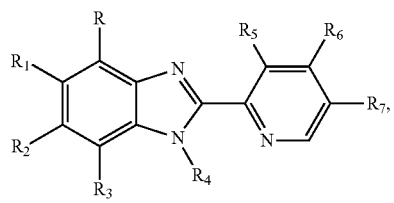

wherein,

R, $R_1$, $R_2$, $R_3$, $R_5$, $R_6$, $R_7$, may be the same or different, and are independently —OH, —$OC_{1-4}$ alkyl, —$OR^a$, trifluoro$C_{1-4}$ alkoxy, —$SC_{1-4}$ alkyl, —S—$R^a$, —$SO_2$—$C_{1-4}$ alkyl, —$SO_2$—$R^a$, —$SOC_{1-4}$ alkyl, —SO—$R^a$, —$SO_2$—NH—$R^b$, —$NR^cR^d$, halo, —$C_{1-4}$ alkyl, —$C_{5-12}$ alkyl, —$C_{2-6}$ alkenyl, —$C_{2-6}$ alkynyl, —$C_{3-6}$ cycloalkyl, or phenyl, benzyl, or monocyclic heteroaryl optionally substituted with $R^b$, —$C_{3-6}$ cycloalkyl optionally containing O, S, N, or Hydrogen, —OC(O)—$R^b$, —OC(O)—$R^b$, —P(O)($OR^b$)$_{1-2}$, —P(S)($OR^b$)$_{1-2}$, —P(O)($NR^cR^d$)$_{1-2}$, —P(S)($NR^cR^d$)$_{1-2}$, —O($CH_2$—$CH_2$—O)$_{1-4}CH_3$, —CN, —COOH, —NO2, —C(O)—$C_{1-4}$ alkyl, or —C(O)—$R^b$, $R^a$ is —$C_{3-6}$ cycloalkyl, —$C_{2-6}$ alkenyl, —$C_{2-6}$ alkynyl, phenyl, benzyl, or monocyclic heteroaryl ring, wherein the phenyl, benzyl, or monocyclic heteroaryl ring is optionally substituted with $R^b$;

$R^b$ is independently H, halo, —OH, —COOH, —$C_{1-4}$ alkyl, $C_{5-12}$ alkyl, phenyl, benzyl, or monocyclic heteroaryl ring, wherein the phenyl, benzyl, or monocyclic heteroaryl ring is optionally substituted with $R^b$, —$C_{2-6}$ alkenyl, —$C_{2-6}$ alkynyl, trifluro$C_{1-4}$ alkoxy, —$OC_{1-4}$ alkyl, —O($CH_2$—$CH_2$—O)$_{1-4}CH_3$, —O-phenyl, —O-benzyl, —$NC_{1-4}$ alkyl, —N-phenyl, and —N— benzyl, —N-monocyclic heteroaryl ring optionally substituted with $R^b$;

$R^C$ and $R^d$ are each independently H, —$C_{1-4}$ alkyl, —$C_{1-4}$ alkyl, —C(O)—$C_{1-4}$ alkyl, —C(O)—$R^e$, —$C_{1-4}$ alkyl-$R^e$, —$SO_2$—$R^a$, —$SO_2$—$C_{1-4}$ alkyl, phenyl, benzyl, or monocyclic heteroaryl ring, wherein the phenyl, benzyl, or monocyclic heteroaryl ring is optionally substituted with $R^b$, and optionally $R^C$ and $R^d$ can be taken together with the nitrogen to which they are attached to form an optionally substituted monocyclic heterocycloalkyl ring optionally containing one or more O, S, N;

$R^e$ is —$C_{3-7}$ heterocycloalkyl ring optionally containing one or more O, S, N; and $R_4$ is —$C_{1-4}$ alkyl, —$C_{5-12}$ alkyl, cyclopropyl, and phenyl, benzyl or monocyclic heteroaryl optionally substituted with $R^b$, —C(O)—$R^b$.

The terms halo, alkyl, etc., are elaborated as follows:

The term halo represents chloro, fluoro, bromo or iodo and also perhaloalkyl groups, including, but not limited to —$CF_3$, —$CF_2H$, and $CH_2CF_3$.

Alkyl refers to straight or branched chain alkyl groups having from methyl, ethyl, n-propyl, isopropyl, butyl, isobutyl, tert-butyl and so on.

Cycloalkyl refers to saturated or partially saturated, monocyclic, polycyclic and spiro polycyclic carbocycle having 3-6 atoms per carbocycle. Illustrative examples of cycloalkyl groups as follows in the properly bonded moieties include:

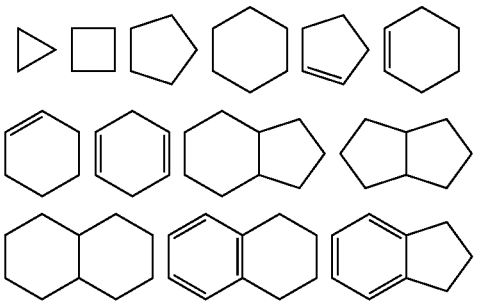

The term heterocycloalkyl refers to monocyclic ring that is saturated or partially saturated and has 4-7 atoms selected from carbon atoms and up to two heteroatoms like nitrogen, sulfur, and oxygen monocyclic, polycyclic and spiro polycyclic carbocycle having 3-6 atoms per carbocycle. Illustrative examples in the form of properly bonded moieties include:

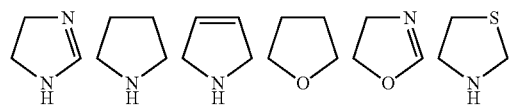

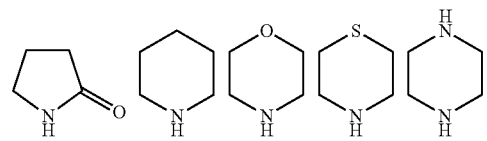

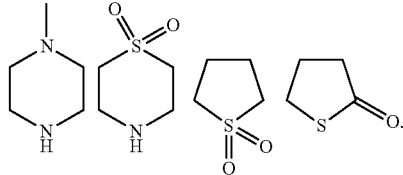

The term heteroaryl refers to monocyclic, fused bicyclic or polycyclic aromatic heterocycle consists of ring atoms selected from carbon atoms and up to four heteroatoms like nitrogen, sulfur, and oxygen. Illustrative examples of heterocyclic rings in the form of properly bonded moieties include:

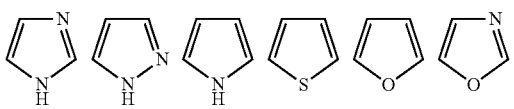

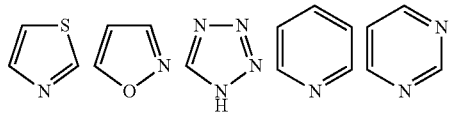

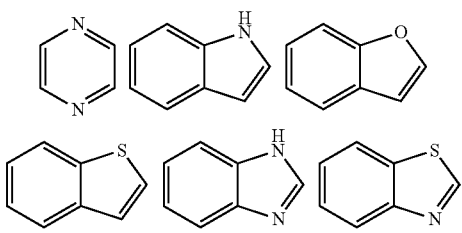

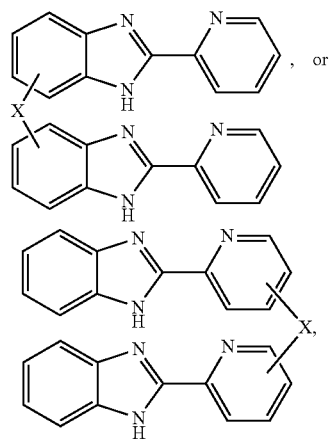

where X is any linker functionality of any length (X=at least one atom), and wherein the compound maintains activity useful for inhibiting CBFβ-SMMHC activity and interaction with Runt, and for treating leukemia.

The present invention provides dimeric compounds having the formula:

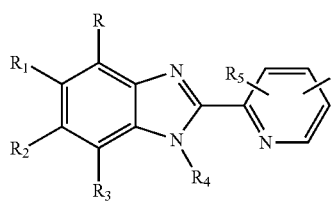

-continued

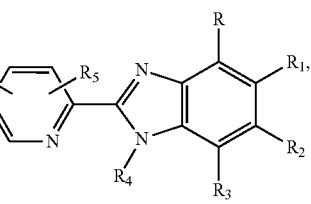

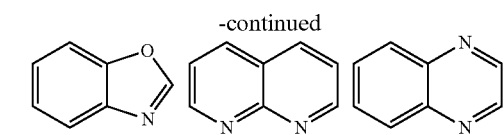

The listed examples of cycloalkyl, heterocycloalkyl, heteroaryl above are not limited and that additional species within the scope of defined terms may also be considered.

In one embodiment, all tautomeric and isomeric forms and mixtures thereof are considered within the scope of the Formula 1 and pharmaceutically acceptable salts, pharmaceutically active metabolites and prodrugs of Formula 1 are encompassed within the present invention. Isotopic labeled compounds of Formula 1, such as deuterium, may improve certain therapeutic properties resulting from metabolic stability. Examples of isotopes that can be incorporated into compounds of Formula 1, include, but are not limited to, $^{2}$H, $^{3}$H, $^{18}$F, $^{14}$C, $^{15}$N, $^{18}$O, $^{31}$P are also included in the invention.

In one aspect, these compounds may be used to form dimers. In one aspect, the dimers are homo-dimers.

In one embodiment, a compound of the invention may have one of the following general structures:

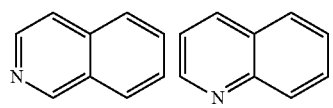

Formula 2 wherein, two monomers can be linked through pyridine rings and each pyridine ring can be monosubstituted ($R_5$ may be H) or di- to poly-substituted depending upon the nature of the reacting species;

$R_5$ is independently m-, and p-substituted to Pyridine —N, H, —OH, —OC$_{1-4}$ alkyl, —OR$^a$, trifluroC$_{1-4}$ alkoxy, —SC$_{1-4}$ alkyl, —S—R$^a$, —SO$_2$—C$_{1-4}$ alkyl, —SO$_2$—R$^a$, —SOC$_{1-4}$ alkyl, —SO—R$^a$, —SO$_2$—NH—R$^b$, —NR$^c$R$^d$, halo, —C$_{1-4}$ alkyl, —C$_{5-12}$ alkyl, —C$_{2-6}$ alkenyl, —C$_{2-6}$ alkynyl, —C$_{3-6}$ cycloalkyl, phenyl, benzyl, or monocyclic heteroaryl ring, wherein the phenyl, benzyl, or monocyclic heteroaryl ring is optionally substituted with R$^b$, —C$_{3-6}$ cycloalkyl optionally containing O, S, N, or Hydrogen, —OC(O)—R$^b$, —OC(O)—R$^b$, —P(O)(OR$^b$)$_{1-2}$, —P(S)(OR$^b$)$_{1-2}$, —P(O)(NR$^c$R$^d$)$_{1-2}$, —P(S)(NR$^c$R$^d$)$_{1-2}$, —O(CH$_2$—CH$_2$—O)$_{1-4}$CH$_3$, —CN, —COOH, —NO2, —C(O)—C$_{1-4}$ alkyl, or —C(O)—R$^b$;

Each X is independently m-, and p-substituted to Pyridine —N, or independently —O, —NH, or —S, where n is an integer of from 1-10;

Y is Oxygen, —NH, or —NR$^f$ where R$^f$ is methyl or ethyl;

R, R$_1$, R$_2$, and R$_3$ are independently —OH, —OC$_{1-4}$ alkyl, —OR$^a$, trifluroC$_{1-4}$ alkoxy, —SC$_{1-4}$ alkyl, —S—R$^a$, —SO$_2$—C$_{1-4}$ alkyl, —SO$_2$—R$^a$, —SOC$_{1-4}$ alkyl, —SO—R$^a$, —SO$_2$—NH—R$^b$, —NR$^c$R$^d$, halo, —C$_{1-4}$ alkyl, —C$_{5-12}$ alkyl, —C$_{2-6}$ alkenyl, —C$_{2-6}$ alkynyl, —C$_{3-6}$ cycloalkyl, phenyl, benzyl, or monocyclic heteroaryl ring, wherein the phenyl, benzyl, or monocyclic heteroaryl ring is optionally substituted with R$^b$, —C$_{3-6}$ cycloalkyl optionally containing O, S, N, or Hydrogen, —OC(O)—R$^b$, —OC (O)—R$^b$, —P(O)(OR$^b$)$_{1-2}$, —P(S)(OR$^b$)$_{1-2}$, —P(O)(NR$^c$R$^d$)$_{1-2}$, —P(S)(NR$^c$R$^d$)$_{1-2}$, —O(CH$_2$—CH$_2$—O)$_{1-4}$CH$_3$, —CN, —COOH, —NO2, —C(O)—C$_{1-4}$ alkyl, or —C(O)—R$^b$;

R$^a$ is —C$_{3-6}$ cycloalkyl, —C$_{2-6}$ alkenyl, —C$_{2-6}$ alkynyl, phenyl, benzyl, or monocyclic heteroaryl ring, wherein the phenyl, benzyl, or monocyclic heteroaryl ring is optionally substituted with R$^b$;

R$^b$ is independently H, halo, —OH, —COOH, —C$_{1-4}$ alkyl, —C$_{5-12}$ alkyl, —C$_{2-6}$ alkenyl, —C$_{2-6}$ alkynyl, trifluroC$_{1-4}$ alkoxy, —OC$_{1-4}$ alkyl, —O(CH$_2$—CH$_2$—O)$_{1-4}$CH$_3$, —O-phenyl, —O-benzyl, —NC$_{1-4}$ alkyl, —N-phenyl, and —N-benzyl, —N-monocyclic heteroaryl ring optionally substituted with R$^b$;

R$^c$ and R$^d$ are each independently H, —C$_{1-4}$ alkyl, —C(O)—C$_{1-4}$ alkyl, —C(O)—R$^e$, —C$_{1-4}$ alkyl-R$^e$, —SO$_2$—R$^a$, —SO$_2$—C$_{1-4}$ alkyl, phenyl, benzyl, or monocyclic heteroaryl ring, wherein the phenyl, benzyl, or monocyclic heteroaryl ring is optionally substituted with R$^b$, and R$^C$ and R$^d$ taken together with the nitrogen to which they are attached optionally form a substituted monocyclic heterocycloalkyl ring optionally containing one or more of O, S, or N;

R$^e$ is —C$_{3-7}$ heterocycloalkyl ring optionally containing one or more O, S, or N;

R$_4$ is —C$_{1-4}$ alkyl, —C$_{5-12}$ alkyl, cyclopropyl, phenyl, benzyl, or monocyclic heteroaryl ring, wherein the phenyl, benzyl, or monocyclic heteroaryl ring is optionally substituted with R$^b$, or —C(O)—R$^b$;

The terms halo, alkyl, etc., are elaborated as follows:

Halo represents chloro, fluoro, bromo or iodo and also perhaloalkyl groups, including CF$_3$, —CF$_2$H, and CH$_2$CF$_3$.

Alkyl refers to straight or branched chain alkyl groups having from methyl, ethyl, n-propyl, isopropyl, butyl, isobutyl, tert-butyl and so on.

The term cycloalkyl refers to saturated or partially saturated, monocyclic, polycyclic and spiro polycyclic carbocycle having 3-6 atoms per carbocycle. Examples of cycloalkyl groups include:

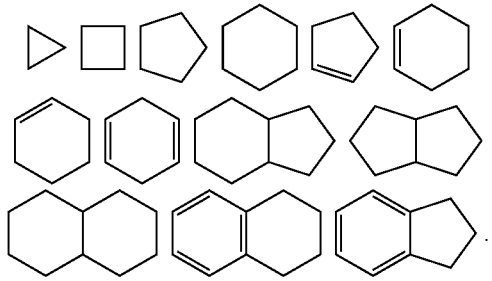

The term heterocycloalkyl refers to monocyclic ring that is saturated or partially saturated and has 4-7 atoms selected from carbon atoms and up to two heteroatoms like nitrogen, sulfur, and oxygen monocyclic, polycyclic and spiro polycyclic carbocycle having 3-6 atoms per carbocycle. Examples in the form of properly bonded moieties include:

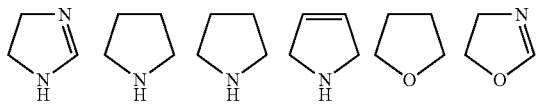

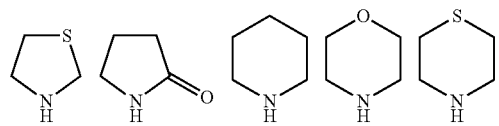

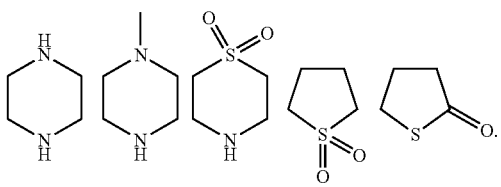

The term heteroaryl refers to monocyclic, fused bicyclic or polycyclic aromatic heterocycle consists of ring atoms selected from carbon atoms and up to two four heteroatoms like nitrogen, sulfur, and oxygen. Examples of heterocyclic rings in the form of properly bonded moieties include, but are not limited to:

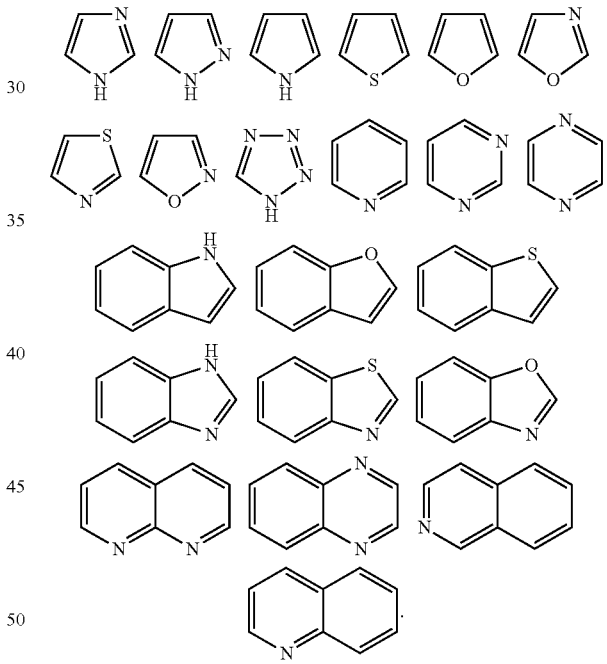

The listed examples of cycloalkyl, heterocycloalkyl, heteroaryl above are not limited and additional species within the scope of defined terms may also be considered.

In one embodiment, all tautomeric and isomeric forms and mixtures thereof are considered with in the scope of the formula and pharmaceutically acceptable salts, pharmaceutically active metabolites and prodrugs of the formula are encompassed with in the present invention. Isotopic labeled of the formula such as deuterium may improve certain therapeutic properties resulting from metabolic stability. Isotopes that can be incorporated into compounds of the formula, including $^2$H, $^3$H, $^{18}$F, $^{14}$C, $^{15}$N, $^{18}$O, and $^{31}$P, are also included in the invention.

The present invention further provides dimeric compounds having the following formulas:

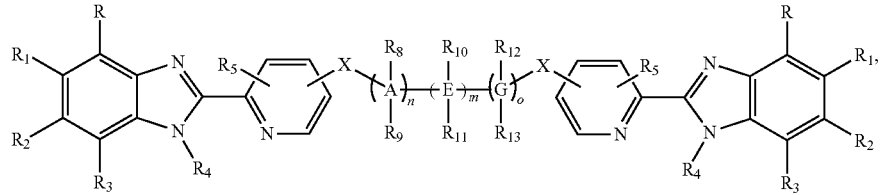
Formula 3

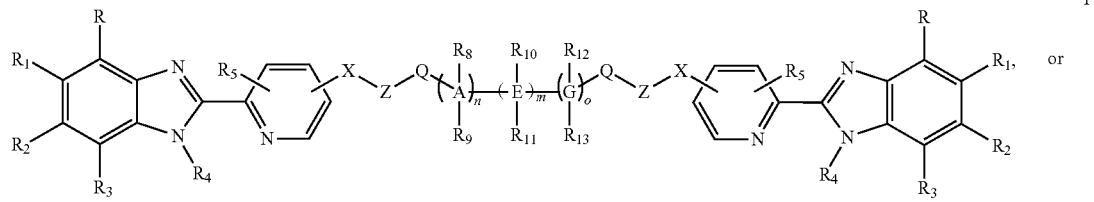
Formula 4

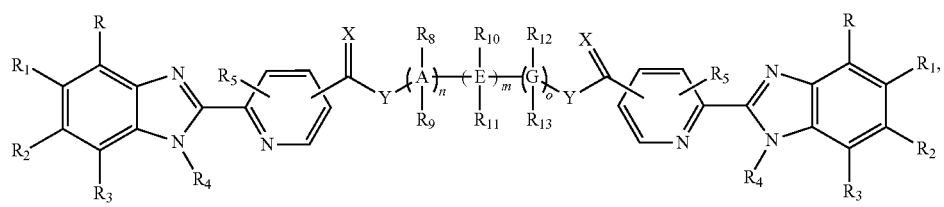
Formula 5 wherein, two monomers can be linked through the pyridine rings and the pyridine rings can be independently monosubstituted ($R_5$ may be H) or di- to poly-substituted depending upon the nature of the reacting species;

$R_5$, of Formulas 3, 4, and 5 is independently m- and p-substituted to Pyridine —N, H, —OH, —OC$_{1-4}$ alkyl, —OR$^a$, trifluroC$_{1-4}$ alkoxy, —SC$_{1-4}$ alkyl, —S—R$^a$, —SO$_2$—C$_{1-4}$ alkyl, —SO$_2$—R$^a$, —SOC$_{1-4}$ alkyl, —SO—R$^a$, —SO$_2$—NH—R$^b$, —NR$^c$R$^d$, halo, —C$_{1-4}$ alkyl, —C$_{5-12}$ alkyl, —C$_{2-6}$ alkenyl, —C$_{2-6}$ alkynyl, —C$_{3-6}$ cycloalkyl, phenyl, benzyl, or monocyclic heteroaryl ring, wherein the phenyl, benzyl, or monocyclic heteroaryl ring is optionally substituted with R$^b$, —C$_{3-6}$ cycloalkyl optionally containing O, S, N, or Hydrogen, —OC(O)—R$^b$, —OC(O)—R$^b$, —P(O)(OR$^b$)$_{1-2}$, —P(S)(OR$^b$)$_{1-2}$, —P(O)(NR$^c$R$^d$)$_{1-2}$, —P(S)(NR$^c$R$^d$)$_{1-2}$, —O(CH$_2$—CH$_2$—O)$_{1-4}$ CH$_3$, —CN, —COOH, —NO2, —C(O)—C$_{1-4}$ alkyl, or —C(O)—R$^b$;

each X is the same or different and each is independently m- and p-substituted to Pyridine —N, and each is independently —O, —NH, or —S, where n=0, 1; m=0, 1; o=0, 1:

Y is Oxygen, —NH, or —NR$^f$ where R$^f$ is methyl or ethyl;

Z is C(O), C(S), P(O)—OR', or P(S)—OR', where R'=H, alkyl, or aryl;

Q may be O, NH, alkyl, aryl, heteroalkyl, or heteroalkylaryl;

A, E, or J are independently C, CH, CH2, CHOR (R or S), N, O, or S;

$R_8$-$R_{13}$ are H or optionally substituted with alkyl, aryl, heteroaryl, alkylaryl, alkylheterocyclic, heteroalkyl, alkylheteroaryl, cycloalkyl, alkylcycloalkyl, or bicycloalkyl;

wherein a chiral A, E, or J is a diastereomer or enantiomer, or diastereomeric mixtures and racemates;

R, $R_1$, $R_2$, and $R_3$ are each independently —OH, —OC$_{1-4}$ alkyl, —OR$^a$, trifluroC$_{1-4}$ alkoxy, —SC$_{1-4}$ alkyl, —S—R$^a$, —SO$_2$—C$_{1-4}$ alkyl, —SO$_2$—R$^a$, —SOC$_{1-4}$ alkyl, —SO—R$^a$, —SO$_2$—NH—R$^b$, —NR$^c$R$^d$, halo, —C$_{1-4}$ alkyl, —C$_{1-4}$ alkyl, —C$_{5-12}$ alkyl, —C$_{2-6}$ alkenyl, —C$_{2-6}$ alkynyl, —C$_{3-6}$ cycloalkyl, phenyl, benzyl, or monocyclic heteroaryl ring, wherein the phenyl, benzyl, or monocyclic heteroaryl ring is optionally substituted with R$^b$, —C$_{3-6}$ cycloalkyl optionally containing O, S, N, Hydrogen, —OC(O)—R$^b$, —OC(O)—R$^b$, —P(O)(OR$^b$)$_{1-2}$, —P(S)(OR$^b$)$_{1-2}$, —P(O)(NR$^c$R$^d$)$_{1-2}$, —P(S)(NR$^c$R$^d$)$_{1-2}$, —O(CH$_2$—CH$_2$—O)$_{1-4}$ CH$_3$, —CN, —COOH, —NO2, —C(O)—C$_{1-4}$ alkyl, and —C(O)—R$^b$;

R$^a$ is —C$_{3-6}$ cycloalkyl, —C$_{2-6}$ alkenyl, —C$_{2-6}$ alkynyl, phenyl, benzyl, or monocyclic heteroaryl ring, wherein the phenyl, benzyl, or monocyclic heteroaryl ring is optionally substituted with R$^b$;

R$^b$ is independently H, halo, —OH, —COOH, —C$_{1-4}$ alkyl, —C$_{5-12}$ alkyl, —C$_{2-6}$ alkenyl, —C$_{2-6}$ alkynyl, trifluroC$_{1-4}$ alkoxy, —OC$_{1-4}$ alkyl, —O(CH$_2$—CH$_2$—O)$_{1-4}$ CH$_3$, —O-phenyl, —O— benzyl, —NC$_{1-4}$ alkyl, —N-phenyl, —N-benzyl, and —N-monocyclic heteroaryl ring, wherein the —N-phenyl, —N-benzyl, and —N-monocyclic heteroaryl ring is optionally substituted with R$^b$;

R$^c$ and R$^d$ are each independently H, —C$_{1-4}$ alkyl, —C(O)—C$_{1-4}$ alkyl, —C(O)—R$^e$, —C$_{1-4}$ alkyl-R$^e$, —SO$_2$—R$^a$, —SO$_2$—C$_{1-4}$ alkyl, phenyl, benzyl, or monocyclic heteroaryl ring, wherein the phenyl, benzyl, or monocyclic heteroaryl ring is optionally substituted with R$^b$, and R$^C$ and R$^d$ together with the nitrogen to which they are attached optionally form a substituted monocyclic heterocycloalkyl ring optionally containing one or more O, S, or N;

R$^e$ is a —C$_{3-7}$ heterocycloalkyl ring, optionally containing one or more of O, S, or N; and $R_4$ is —C$_{1-4}$ alkyl, —C$_{5-12}$ alkyl, cyclopropyl, phenyl, benzyl, or monocyclic heteroaryl ring, wherein the phenyl, benzyl, or monocyclic heteroaryl ring is optionally substituted with R$^b$.

The terms like halo, alkyl, etc., are elaborated as follows:

The term halo represents chloro, fluoro, bromo or iodo and also perhaloalkyl groups like —CF$_3$, —CF$_2$H, CH$_2$CF$_3$.

Alkyl refers to straight or branched chain alkyl groups having from methyl, ethyl, n-propyl, isopropyl, butyl, isobutyl, tert-butyl and so on.

The term cycloalkyl refers to saturated or partially saturated, monocyclic, polycyclic and spiro polycyclic carbocycle having 3-6 atoms per carbocycle. Examples of cycloalkyl groups, include, but are not limited to, the properly bonded moieties below:

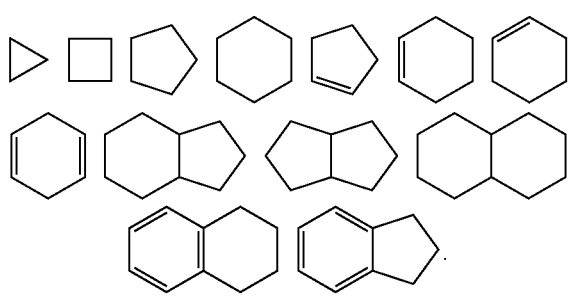

The term heterocycloalkyl refers to monocyclic ring that is saturated or partially saturated and has 4-7 atoms selected from carbon atoms and up to two heteroatoms like nitrogen, sulfur, and oxygen monocyclic, polycyclic and spiro polycyclic carbocycle having 3-6 atoms per carbocycle. Examples in the form of properly bonded moieties, include, but are not limited to:

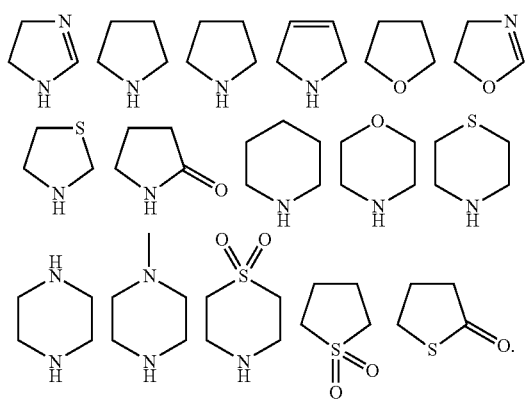

The term heteroaryl refers to monocyclic, fused bicyclic or polycyclic aromatic heterocycle consists of ring atoms selected from carbon atoms and up to two four heteroatoms like nitrogen, sulfur, and oxygen. Examples of heterocyclic rings in the form of properly bonded moieties include, but are not limited to:

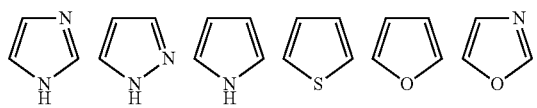

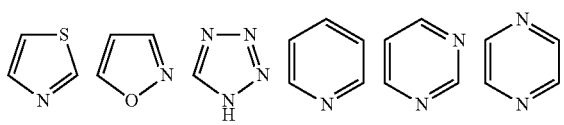

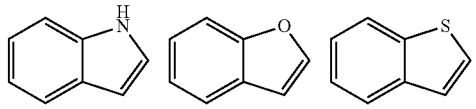

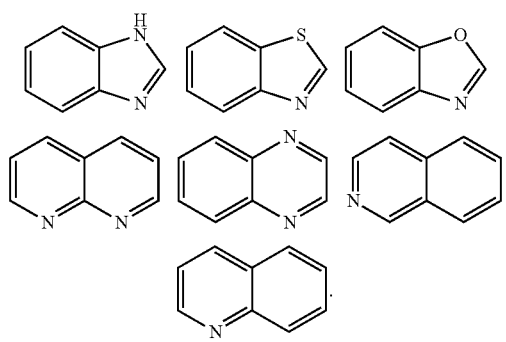

The listed examples of cycloalkyl, heterocycloalkyl, heteroaryl above are not limited and that additional species within the scope of defined terms may also be considered.

In one embodiment, all tautomeric and isomeric forms and mixtures thereof are considered with in the scope of the Formula 1 and pharmaceutically acceptable salts, pharmaceutically active metabolites and prodrugs of Formula 1 are encompassed with in the present invention. Isotopic labeled of Formula 1 such as deuterium may improve certain therapeutic properties resulting from metabolic stability. Examples of isotopes $^2H$, $^3H$, $^{18}F$, $^{14}C$, $^{15}N$, $^{18}O$, $^{31}P$ that can be incorporated into compounds of Formula 1 are also included in the invention.

The present invention further provides dimeric compounds having the formula:

Formula 6

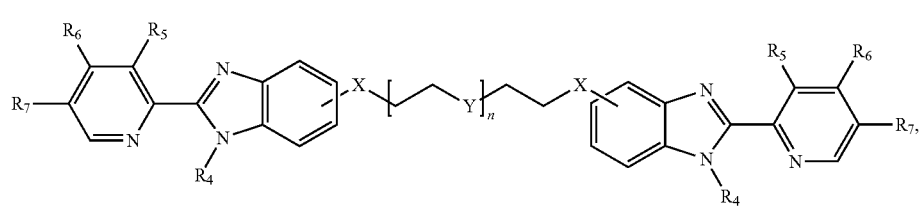

wherein, two monomers can be linked through the benzimidazole rings, or the benzimidazole rings can mono or di- to poly-substituted depending upon the nature of the reacting species;

each X is independently 4-, 5-, or 6-substituted and each X is independently —O, —NH, or —S, where "n" is an integer of from 1-10;

Y is Oxygen, —NH, or —NR$^f$, where R$^f$ is methyl or ethyl;

$R_5$, $R_6$, and $R_7$ are independently —OH, —OC$_{1-4}$ alkyl, —OR$^a$, trifluroC$_{1-4}$ alkoxy, —SC$_{1-4}$ alkyl, —S—R$^a$, —SO$_2$—C$_{1-4}$ alkyl, —SO$_2$—R$^a$, —SOC$_{1-4}$ alkyl, —SO—R$^a$, —SO$_2$—NH—R$^b$, —NR$^c$R$^d$, halo, —C$_{1-4}$ alkyl, —C$_{5-12}$ alkyl, —C$_{2-6}$ alkenyl, —C$_{2-6}$ alkynyl, —C$_{3-6}$ cycloalkyl, phenyl, benzyl, or monocyclic heteroaryl ring, wherein the phenyl, benzyl, or monocyclic heteroaryl ring is optionally substituted with R$^b$, —C$_{3-6}$ cycloalkyl optionally containing O, S, N, or Hydrogen, —OC(O)—R$^b$, —OC(O)—R$^b$, —P(O)(OR$^b$)$_{1-2}$, —P(S)(OR$^b$)$_{1-2}$, —P(O)(NR$^c$R$^d$)$_{1-2}$, —P(S)(NR$^c$R$^d$)$_{1-2}$, —O(CH$_2$—CH$_2$—O)$_{1-4}$CH$_3$, —CN, —COOH, —NO2, —C(O)—C$_{1-4}$ alkyl, or —C(O)—R$^b$;

R$^a$ is —C$_{3-6}$ cycloalkyl, —C$_{2-6}$ alkenyl or optimally substituted alkenyl, —C$_{2-6}$ alkynyl or optimally substituted alkynyl, phenyl, benzyl, or monocyclic heteroaryl ring, wherein the phenyl, benzyl, or monocyclic heteroaryl ring is optionally substituted with R$^b$;

R$^b$ is independently H, halo, —OH, —COOH, —C$_{1-4}$ alkyl, —C$_{5-12}$ alkyl, —C$_{2-6}$ alkenyl, —C$_{2-6}$ alkynyl, trifluroC$_{1-4}$ alkoxy, —OC$_{1-4}$ alkyl, —O(CH$_2$—CH$_2$—O)$_{1-4}$CH$_3$, —O-phenyl, —O-benzyl, —NC$_{1-4}$ alkyl, and —N-phenyl, —N-benzyl, or —N-monocyclic heteroaryl ring, wherein the —N-phenyl, —N-benzyl, or —N-monocyclic heteroaryl ring is optionally substituted with R$^b$;

R$^c$ and R$^d$ are each independently H, —C$_{1-4}$ alkyl, —C(O)—C$_{1-4}$ alkyl, —C(O)—R$^e$, —C$_{1-4}$ alkyl-R$^e$, —SO$_2$—R$^a$, —SO$_2$—C$_{1-4}$ alkyl, phenyl, benzyl, or monocyclic heteroaryl ring, wherein the phenyl, benzyl, or monocyclic heteroaryl ring is optionally substituted with R$^b$, and R$^c$ and R$^d$ taken together with the nitrogen to which they are attached optionally form a substituted monocyclic heterocycloalkyl ring optionally containing one or more of O, S, or N;

R$^e$ is —C$_{3-7}$ heterocycloalkyl ring optionally containing one or more of O, S, or N; and $R_4$ is —C$_{1-4}$ alkyl, —C$_{5-12}$ alkyl, cyclopropyl, —C(O)—R$^b$, phenyl, benzyl, or monocyclic heteroaryl ring, wherein the phenyl, benzyl, or monocyclic heteroaryl ring is optionally substituted with R$^b$.

Terms like halo, alkyl, etc., are elaborated as follows:

The term halo represents chloro, fluoro, bromo or iodo and also perhaloalkyl groups, including, but not limited to, —CF$_3$, —CF$_2$H, and CH$_2$CF$_3$.

Alkyl refers to straight or branched chain alkyl groups having from methyl, ethyl, n-propyl, isopropyl, butyl, isobutyl, tert-butyl and so on.

The term cycloalkyl refers to saturated or partially saturated, monocyclic, polycyclic and spiro polycyclic carbocycle having 3-6 atoms per carbocycle. Examples of cycloalkyl groups include, but are not limited to, the properly bonded moieties.

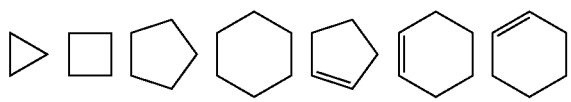

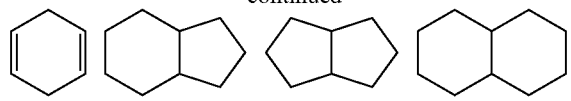

The term heterocycloalkyl refers to monocyclic ring that is saturated or partially saturated and has 4-7 atoms selected from carbon atoms and up to two heteroatoms like nitrogen, sulfur, and oxygen monocyclic, polycyclic and spiro polycyclic carbocycle having 3-6 atoms per carbocycle. Examples in the form of properly bonded moieties include, but are not limited to:

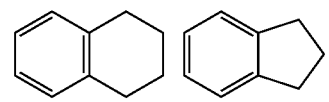

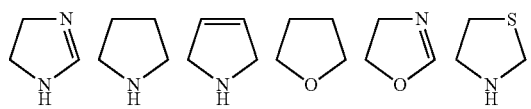

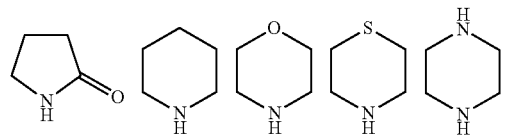

The term heteroaryl refers to monocyclic, fused bicyclic or polycyclic aromatic heterocycle consists of ring atoms selected from carbon atoms and up to two four heteroatoms like nitrogen, sulfur, and oxygen. Examples of heterocyclic rings in the form of properly bonded moieties include, but are not limited to:

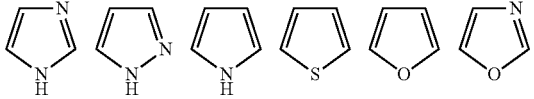

-continued

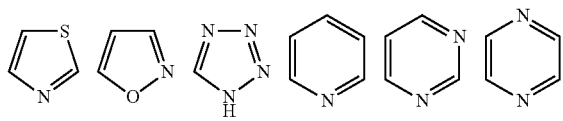

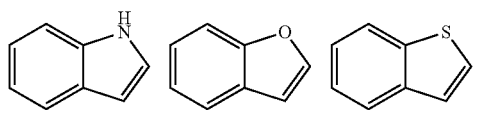

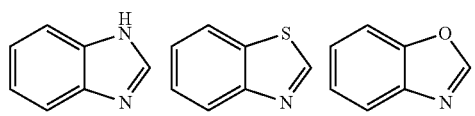

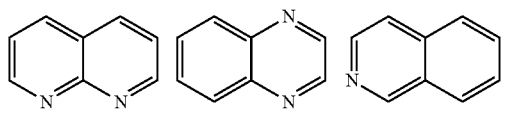

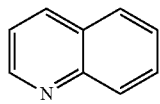

The listed examples of cycloalkyl, heterocycloalkyl, heteroaryl above are not limited and that additional species within the scope of defined terms may also be considered.

In one embodiment, all tautomeric and isomeric forms and mixtures thereof are considered with in the scope of the Formula 1 and pharmaceutically acceptable salts, pharmaceutically active metabolites and prodrugs of Formula 1 are encompassed with in the present invention. Isotopic labeled of Formula 1 such as deuterium may improve certain therapeutic properties resulting from metabolic stability. Examples of isotopes that can be incorporated into compounds of Formula 1 include, but are not limited to $^2$H, $^3$H, $^{18}$F, $^{14}$C, $^{15}$N, $^{18}$O, and $^{31}$P.

In one embodiment, a dimer of the invention has the following formula:

Formula 7 wherein $R_1$, $R_2$, $R_3$, $R_4$, $R_5$, and $R_6$ are each independently selected from hydrogen, —OH, —COOH, —OCNH$_2$, —OCH$_3$, halogen, —OC$_2$H$_5$, —SCH$_3$, —OCF$_3$, —CF$_3$N, O, S,

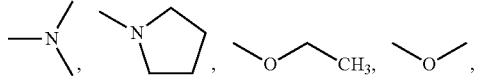

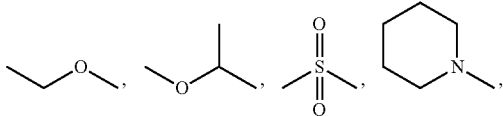

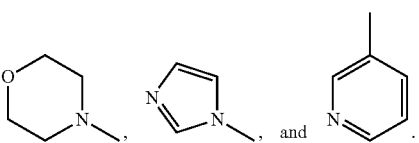

In one aspect, X is any linker functionality of any length, wherein the compound maintains activity as described herein, including inhibiting proliferation of inv(16) leukemia cells and for treating leukemia. In one aspect, the X linkers include, but are not limited to:

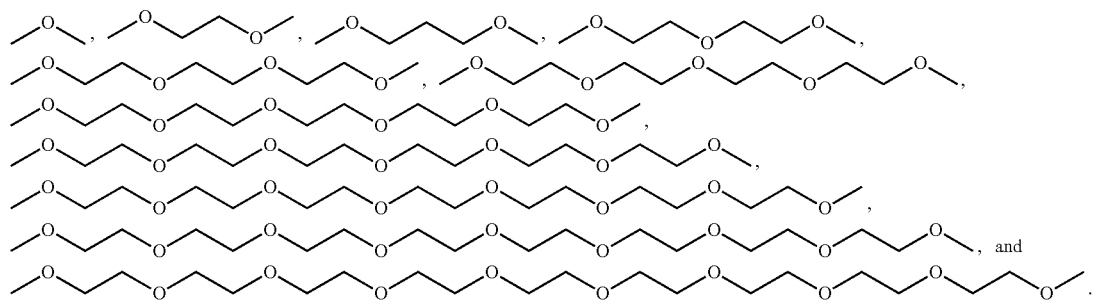

In one aspect, X is from 1 to about 40 atoms.

In one embodiment, a dimer of the invention has the following formula:

Formula 8

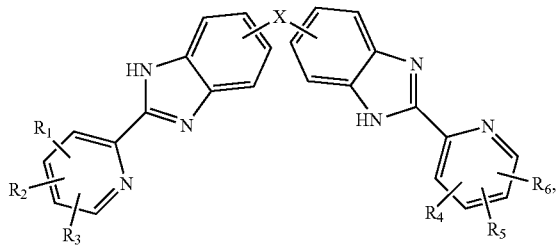

wherein $R_1$, $R_2$, $R_3$, $R_4$, $R_5$, and $R_6$ are each independently selected from hydrogen, —OH, —COOH, —OCNH$_2$, —OCH$_3$, halogen, —OC$_2$H$_5$, —SCH$_3$, —OCF$_3$, —CF$_3$N, O, S,

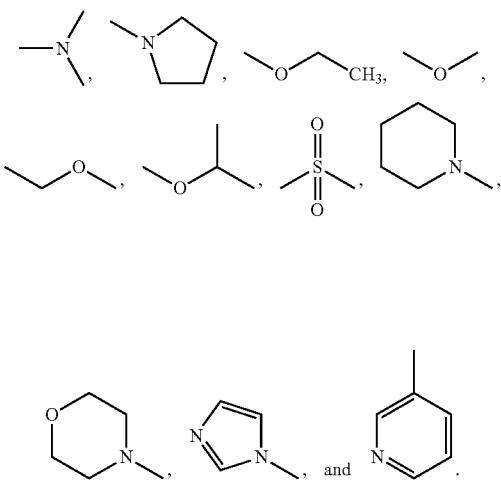

In one aspect, X is any linker functionality of any length, wherein the compound maintains activity as described herein, including inhibiting proliferation of inv(16) leukemia cells and for treating leukemia. In one aspect, the X linkers include, but are not limited to:

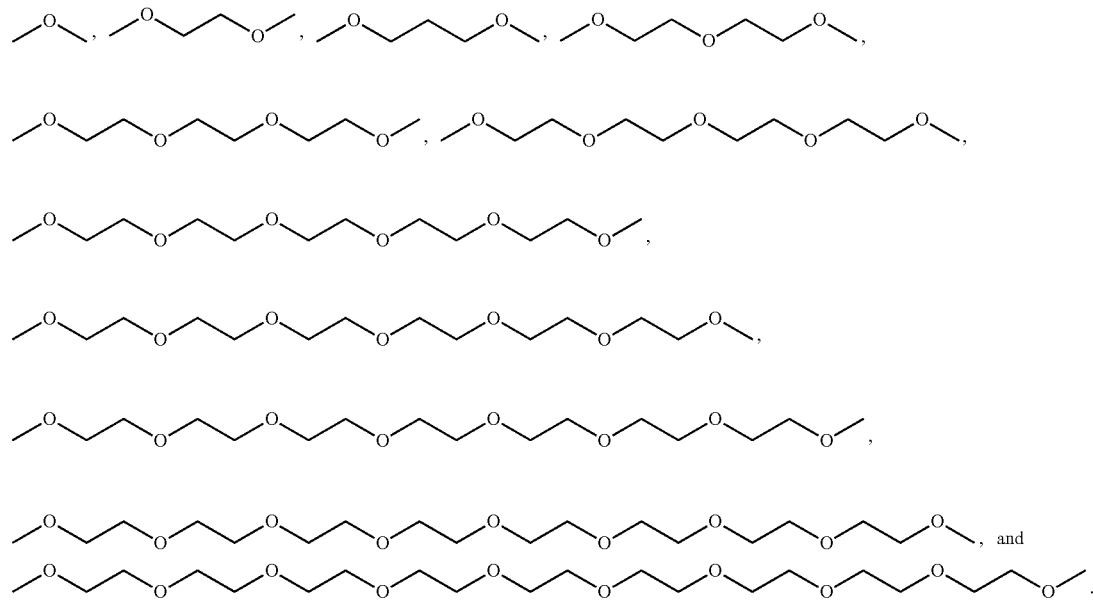

In one aspect, X is from 1 to about 40 atoms.
Useful side chains of the invention include, but are not limited to:
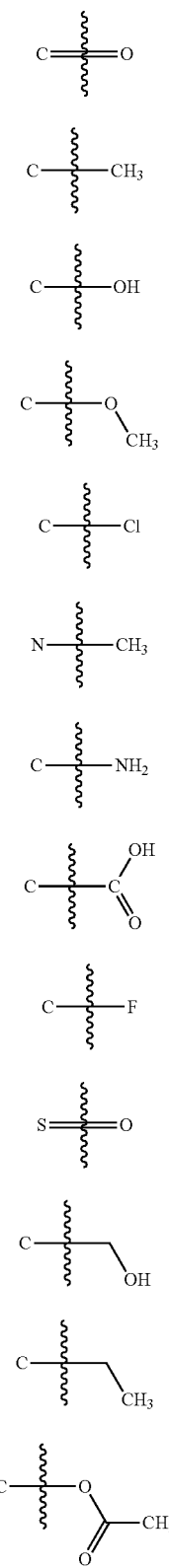
1 (3545)
2 (3125)
3 (2566)
4 (916)
5 (823)
6 (719)
7 (549)
8 (454)
9 (355)
10 (331)
11 (235)
12 (214)
13 (155)
-continued
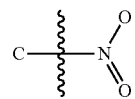
14 (137)
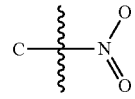
15 (108)
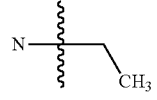
16 (93)
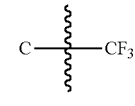
17 (85)
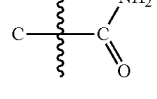
18 (84)
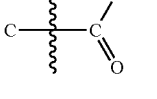
19 (81)
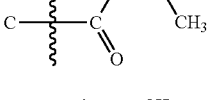
20 (76)
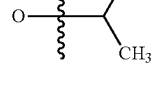
21 (74)
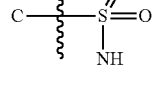
22 (72)
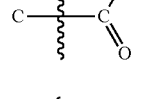
23 (72)
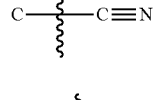
24 (63)
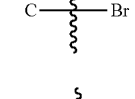
25 (62)
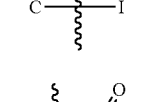
26 (59)
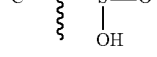
27 (55)

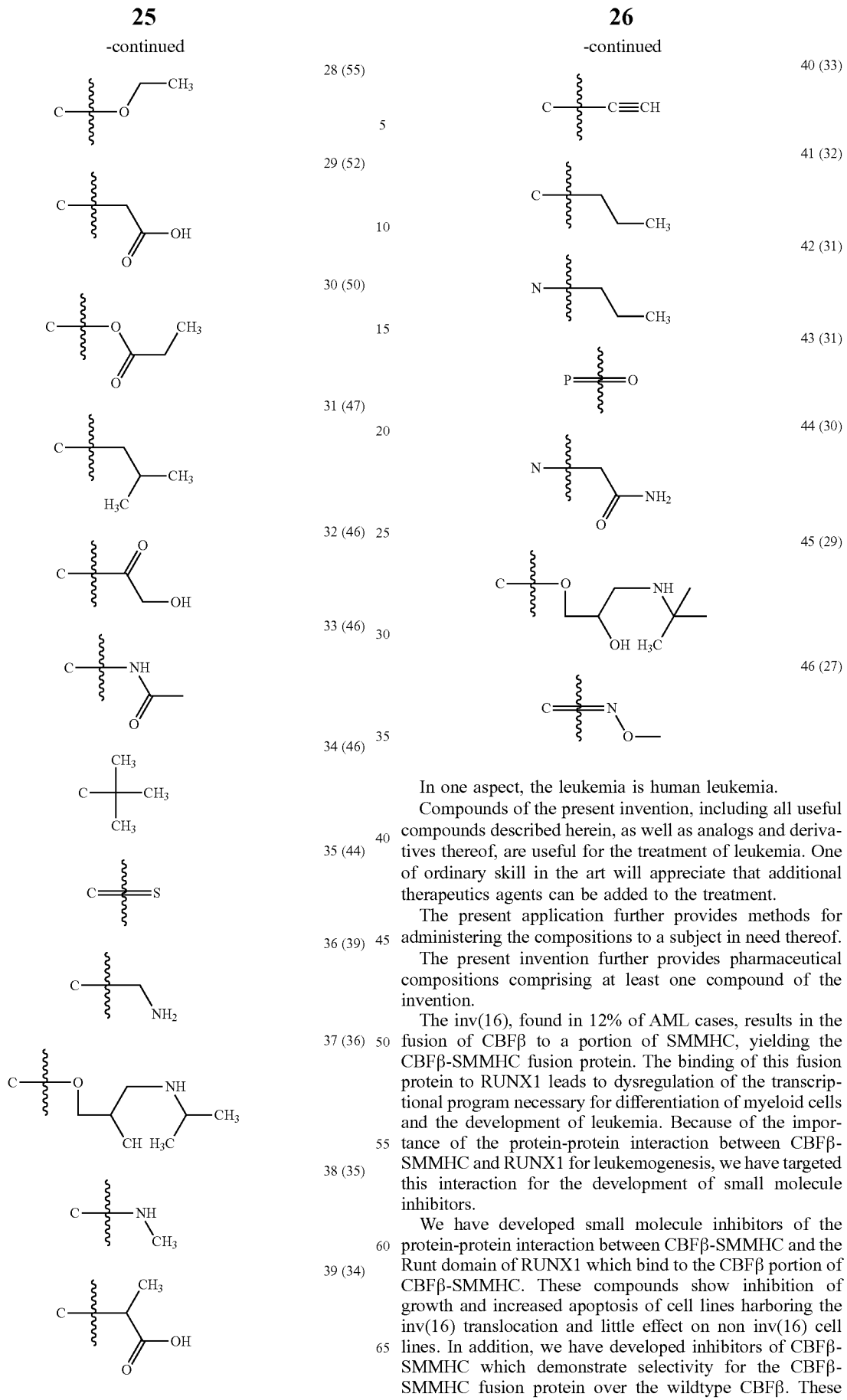

In one aspect, the leukemia is human leukemia.

Compounds of the present invention, including all useful compounds described herein, as well as analogs and derivatives thereof, are useful for the treatment of leukemia. One of ordinary skill in the art will appreciate that additional therapeutics agents can be added to the treatment.

The present application further provides methods for administering the compositions to a subject in need thereof.

The present invention further provides pharmaceutical compositions comprising at least one compound of the invention.

The inv(16), found in 12% of AML cases, results in the fusion of CBFβ to a portion of SMMHC, yielding the CBFβ-SMMHC fusion protein. The binding of this fusion protein to RUNX1 leads to dysregulation of the transcriptional program necessary for differentiation of myeloid cells and the development of leukemia. Because of the importance of the protein-protein interaction between CBFβ-SMMHC and RUNX1 for leukemogenesis, we have targeted this interaction for the development of small molecule inhibitors.

We have developed small molecule inhibitors of the protein-protein interaction between CBFβ-SMMHC and the Runt domain of RUNX1 which bind to the CBFβ portion of CBFβ-SMMHC. These compounds show inhibition of growth and increased apoptosis of cell lines harboring the inv(16) translocation and little effect on non inv(16) cell lines. In addition, we have developed inhibitors of CBFβ-SMMHC which demonstrate selectivity for the CBFβ-SMMHC fusion protein over the wildtype CBFβ. These inhibitors show increased potency against inv(16) cell lines and no effect on non inv(16) cell lines.

Currently, standard cytotoxic chemotherapy is used for the treatment of inv(16) leukemia. While reasonably well tolerated by younger patients, this is not well tolerated by the predominantly older patient population afflicted by this disease. More importantly, approximately 60% of inv(16) patients relapse and die within 5 years, indicating a substantial relapse rate. This is almost certainly the result of not eradicating the leukemia stem cell population when treating with standard chemotherapy, allowing the disease to recur. As it is known that CBFβ-SMMHC changes the gene expression profile of cells to something that is more stem cell like, it is clear that CBFβ-SMMHC is a driver of the leukemia stem cell phenotype. Therefore, it is highly likely that direct inhibition of the action of CBFβ-SMMHC can alter this expression profile and therefore be a more effective therapeutic approach either alone or in combination with cytotoxic chemotherapy.

Useful monomeric compounds of the invention (see Table 1), include, but are not limited to the following compounds, as well as biologically active dimers, derivatives, and analogs thereof: NCI-320656, AI-4-57 (LD-1-11C), AI-4-52, LD-1-29 (AI-10-54), AI-4-42, AI-4-70 (LD-2-21), LD-1-127, AI-10-61, LD-1-138, AI-10-35, AI-10-37, AI-10-47, LD-2-11, AI-4-46, LD-1-23, LD-1-37, LD-1-31, LD-1-33, AI-4-43, LD-1-39, LD-2-79, AI-10-51, AI-4-49, LD-2-23, AI-4-47, AI-4-48, LD-2-63, AI-10-83, AI-10-82, AI-10-3, AI-10-88, AI-10-57, AI-10-70, AI-10-97, AI-10-96, AI-4-61 (AI-10-52), AI-10-101, AI-10-11, AI-10-87, AI-10-53, AI-10-69, AI-10-63, AI-10-65, AI-10-64, LD-2-101, AI-10-77, LD-2-91, AI-4-55, LD-2-89, LD-2-99, LD-1-75, AI-4-53, AI-4-55, LD-1-73, AI-4-44, and AI-4-45.

The monomeric compounds use herein have the following structures:

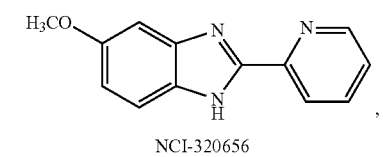

NCI-320656

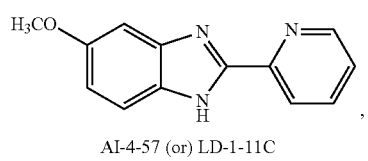

AI-4-57 (or) LD-1-11C

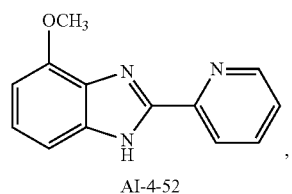

AI-4-52

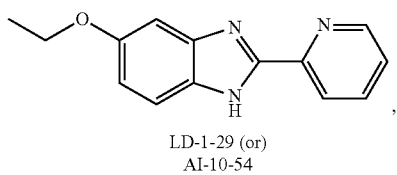

LD-1-29 (or) AI-10-54

-continued

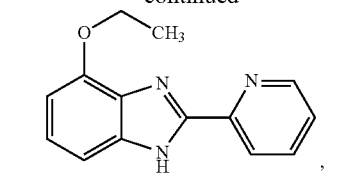

AI-4-42

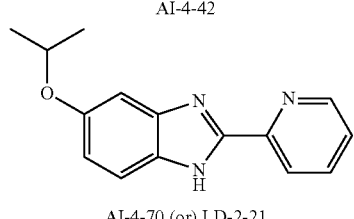

AI-4-70 (or) LD-2-21

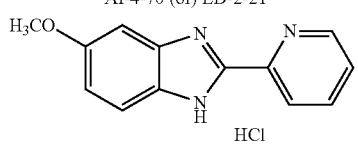

LD-1-127

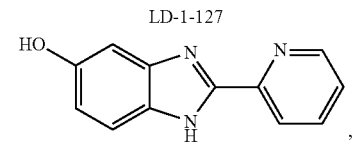

AI-10-61

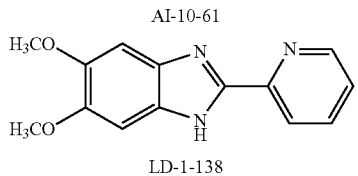

LD-1-138

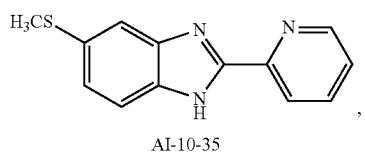

AI-10-35

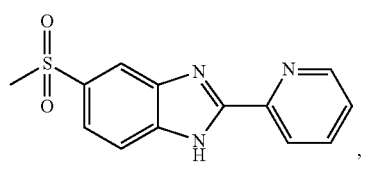

AI-10-37

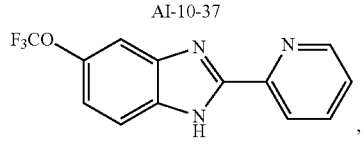

AI-10-47

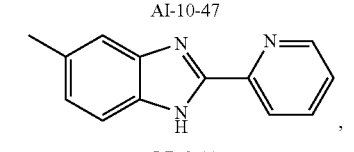

LD-2-11

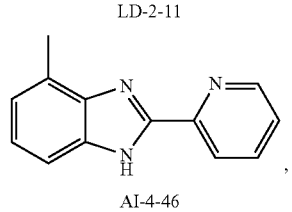

AI-4-46

LD-1-23, LD-1-37, LD-1-31, LD-1-33, AI-4-43, LD-1-39, LD-2-79, AI-10-51, AI-4-49, LD-2-23,

AI-4-47, AI-4-48, LD-2-63, AI-10-83, AI-10-82, AI-10-3, AI-10-88, AI-10-57, AI-10-70,

-continued

AI-10-97

AI-10-96

AI-4-61 (or)
AI-10-52

AI-10-101

AI-10-11

AI-10-87

AI-10-53

AI-10-69

AI-10-63

-continued

AI-10-65

AI-10-64

LD-2-101

AI-10-77

LD-2-91

AI-4-55

LD-2-89

LD-2-99

LD-1-75

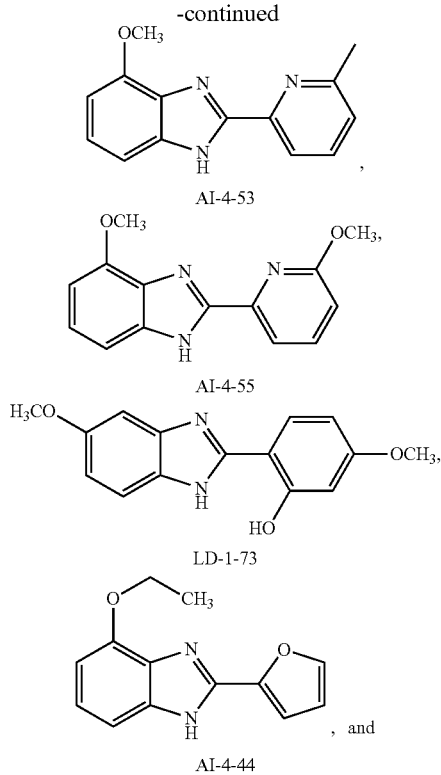

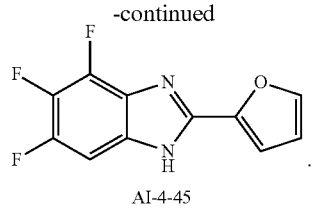

The above-identified monomers include known monomers as well as novel monomers disclosed herein. The novel monomers include: AI-4-70 (LD-2-21), LD-1-138, AI-10-35, AI-10-37, AI-10-47, LD-1-33, AI-4-43, LD-1-39, AI-10-51, AI-4-49, AI-4-48, AI-10-83, AI-10-82, AI-10-3, AI-10-70, AI-10-97, AI-10-96, AI-4-61 (AI-10-52), AI-10-101, AI-10-11, AI-10-87, AI-10-53, AI-10-69, AI-10-63, AI-10-65, AI-10-64, LD-2-101, AI-10-77, LD-2-91, AI-4-55, LD-2-99, LD-1-75, AI-4-53, AI-4-55, LD-1-73, AI-4-44, and AI-4-45.

The present invention further provides dimers of the above-identified monomeric compounds. In one aspect, the dimers are homo-dimers.

Useful dimeric compounds of the invention, include, but are not limited to the following compounds, as well as biologically active derivatives and analogs thereof:

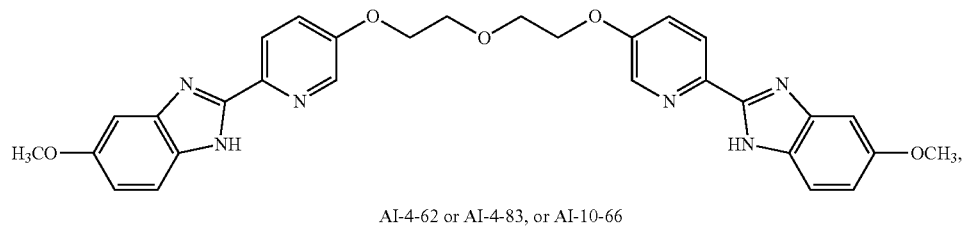

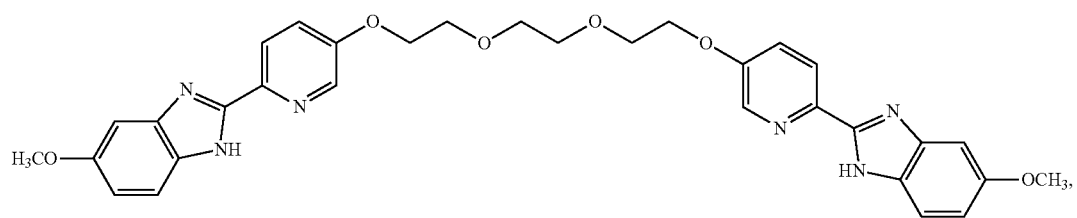

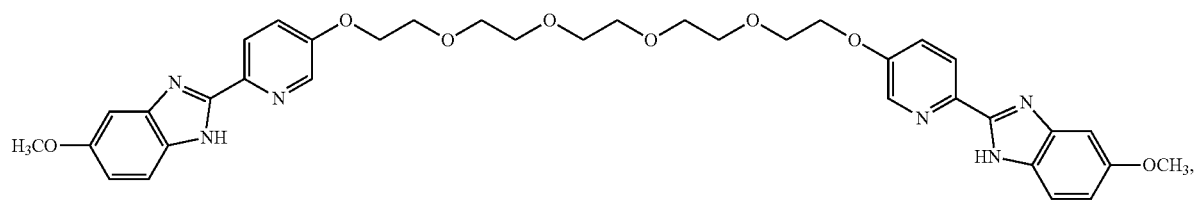

-continued
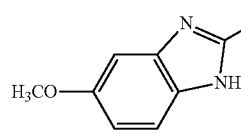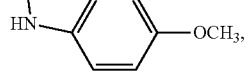
AI-10-19
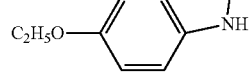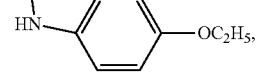
AI-10-42
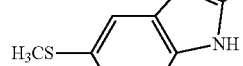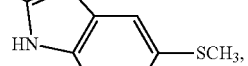
AI-10-99
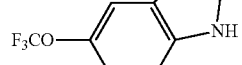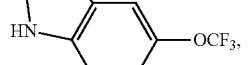
AI-10-49
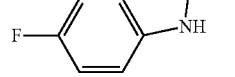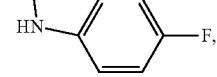
AI-10-81
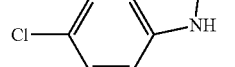
AI-10-55
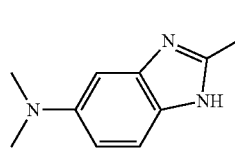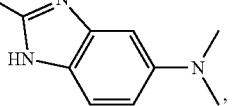
AI-10-21

-continued

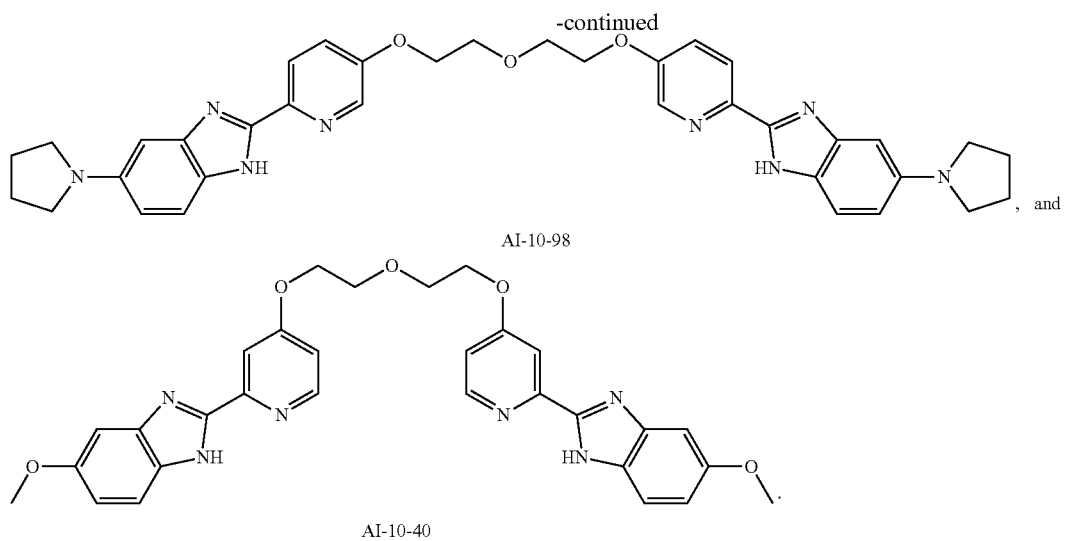

AI-10-98, and

AI-10-40.

The present invention provides compositions and methods useful for making compounds of the invention, as described in the Examples, including FIG. 6. One of ordinary skill in the art will appreciate that modifications to the scheme can be made to synthesize a particular compound of interest.

BRIEF DESCRIPTION OF THE DRAWINGS

FIGS. 10A and 10B, depicts graphically the effects of a dimeric inhibitor on inv(16) repression using a luciferase reporter assay. Top (10A): Effect of AI-4-83 on repression by inv(16) measured using a luciferase reporter assay. A dose response of 0, 2.5, 5.0, and 10 μM was tested on MEF5E-4D3, MEF5E-4D3-1H2, MEF5E-4D3-4G6, and MEF5E-4D3-4G9. Bottom (10B): Effect of inv(16) siRNA on repression by inv(16) measured using the same luciferase reporter assay. −siRNA—left bar; +siRNA—right bar; Tested were 5E-4D3, 5E-4D3-1H2, 5E-4D3-4G6, and 5E-4D3-4G9. The ordinate represents relative luciferase activity.

DETAILED DESCRIPTION

Definitions

Figure 1:
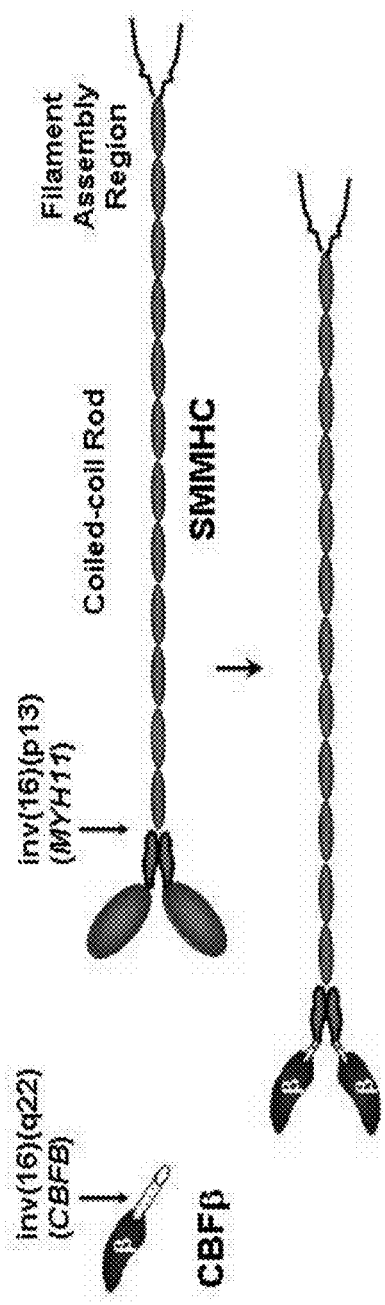
FIG. 1. Schematic representation of the inv(16) protein product, CBFβ-SMMHC.

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for radicals, substituents, and ranges are for illustration only; they do not exclude other defined values or other values within defined ranges for the radicals and substituents.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

The term "adult" as used herein, is meant to refer to any non-embryonic or non-juvenile subject. For example the term "adult adipose tissue stem cell," refers to an adipose stem cell, other than that obtained from an embryo or juvenile subject.

As used herein, an "agonist" is a composition of matter that, when administered to a mammal such as a human, enhances or extends a biological activity of interest. Such effect may be direct or indirect.

A disease or disorder is "alleviated" if the severity of a symptom of the disease, condition, or disorder, or the frequency with which such a symptom is experienced by a subject, or both, are reduced.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

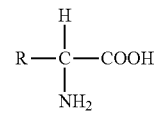

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter that when administered to a mammal such as a human, inhibits or impedes a biological activity attributable to the level or presence of an endogenous compound in the mammal. Such effect may be direct or indirect.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, an "analog" of a chemical compound is a compound that, by way of example, resembles another in structure but is not necessarily an isomer (e.g., 5-fluorouracil is an analog of thymine).

"Anti-proliferative," as used herein, refers to the ability of a compound to impede or inhibit cell proliferation. As such, the compound may act directly on a cell or may act indirectly. For example, in the context of cancer, a cancer cell can be inhibited from proliferating by depriving it of blood supply. The term "anti-proliferative" does not refer to a particular mechanism by which proliferation is inhibited or impeded.

As used herein the term "anti-tumor agent" relates to agents known in the art that have been demonstrated to have utility for treating neoplastic disease. For example, antitumor agents include, but are not limited to, antibodies, toxins, chemotherapeutics, enzymes, cytokines, radionuclides, photodynamic agents, and angiogenesis inhibitors. Toxins include ricin A chain, mutant *Pseudomonas* exotoxins, diphtheria toxoid, streptonigrin, boamycin, saporin, gelonin, and pokeweed antiviral protein. Chemotherapeutics include 5-fluorouracil (5-FU), daunorubicin, cisplatinum, bleomycin, melphalan, taxol, tamoxifen, mitomycin-C, and methotrexate as well as any of the compounds described in U.S. Pat. No. 6,372,719 (the disclosure of which is incorporated herein by reference) as being chemotherapeutic agents. Radionuclides include radiometals. Photodynamic agents include porphyrins and their derivatives.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "biological sample," as used herein, refers to samples obtained from a living organism, including skin, hair, tissue, blood, plasma, cells, sweat, and urine.

As used herein, the term "biologically active fragments" or "bioactive fragment" of the polypeptides encompasses natural or synthetic portions of the full-length protein that are capable of specific binding to their natural ligand or of performing the function of the protein.

A "biomarker" is a specific biochemical in the body which has a particular molecular feature that makes it useful for measuring the progress of disease or the effects of treatment, or for measuring a process of interest.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize), as well as any of a number of characteristic structural and/or molecular features. A "cancerous" or "malignant cell" is understood as a cell having specific structural properties, lacking differentiation and being capable of invasion and metastasis. Examples of cancers are, breast, lung, brain, bone, liver, kidney, colon, and prostate cancer. (see DeVita, V. et al. (eds.), 2001, Cancer Principles and Practice of Oncology, 6th. Ed., Lippincott Williams & Wilkins, Philadelphia, Pa.; this reference is herein incorporated by reference in its entirety for all purposes).

"Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "complex", as used herein in reference to proteins, refers to binding or interaction of two or more proteins. Complex formation or interaction can include such things as binding, changes in tertiary structure, and modification of one protein by another, such as phosphorylation.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:
I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

The term "cancer," as used herein, is defined as proliferation of cells whose unique trait—loss of normal controls—results new characteristics such as unregulated growth, lack of differentiation, local tissue invasion, and metastasis. Examples include, but are not limited to, breast cancer, prostate cancer, ovarian cancer, cervical cancer, skin cancer, melanoma, pancreatic cancer, colorectal cancer, renal cancer, leukemia, non small cell carcinoma, and lung cancer.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting cancer or a risk or propensity for development of cancer, for the types of cancer encompassed by the invention. In any method of diagnosis exist false positives and false negatives. Any one method of diagnosis does not provide 100% accuracy.

A "disease" is a state of health of an animal wherein the subject cannot maintain homeostasis, and wherein if the disease is not ameliorated then the subject's health continues to deteriorate. In contrast, a "disorder" in an subject is a state of health in which the animal is able to maintain homeostasis, but in which the subject's state of health is less favorable than it would be in the absence of the disorder. Left untreated, a disorder does not necessarily cause a further decrease in the subject's state of health.

As used herein, an "effective amount" means an amount sufficient to produce a selected effect, such as alleviating symptoms of a disease or disorder, preferably in treating an inv(16) leukemia. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly 5 amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound of the invention to reduce or impede a described function, such as cell proliferation, tumor growth, or angiogenesis. Preferably, inhibition is by at least 10%, more preferably by at least 25%, even more preferably by at least 50%, and most preferably, the function is inhibited by at least 75%.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, *Antibodies, A Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

By "presensitization" is meant pre-administration of at least one innate immune system stimulator prior to challenge with a pathogenic agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prophylactic" treatment is a treatment administered to a subject who does not exhibit signs of a disease or injury or exhibits only early signs of the disease or injury for the purpose of decreasing the risk of developing pathology associated with the disease or injury.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates. The terms "protein pathway" and "protein regulatory pathway" are used interchangeably herein.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

The term "standard," as used herein, refers to something used for comparison. For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of diagnosis or treatment is a mammal, including a human.

As used herein, a "subject in need thereof" is a patient, animal, mammal, or human, who will benefit from the method of this invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. AOptionally substituted aryl@ includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

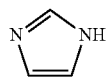

is understood to represent a mixture of the structures:

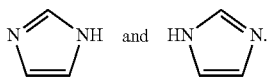

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Embodiments

The present invention provides compositions and methods useful for inhibiting inv(16) leukemia cell proliferation and for increasing apoptosis in inv(16) leukemia cells. The method encompasses directly inhibiting protein-protein interactions.

The compositions include known and new compounds useful for practicing the methods of the invention, as well as methods for making the compounds. Techniques for preparing analogs, derivatives, and modifications of the generic structures of the invention are known in the art or described herein. Some examples of diseases which may be treated according to the methods of the invention are discussed herein or are known in the art. The present invention further provides methods for testing compounds of the invention. Other methods for testing compounds discovered using the methods of the invention are either described herein or are known in the art.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds have the formulas of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of a formula of the invention, in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple injections or by direct or topical application.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising at least one compound identified in the invention and an instructional material which describes administering the compound or a composition comprising the compound to a cell or a subject. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention. Therefore, the examples should be construed to encompass any and all variations which become evident as a result of the teaching provided herein.

Examples

FRET Assay

We have developed effective assays to monitor the inhibition of CBFβ-SMMHC binding to the Runt domain (as well as for CBFβ binding to the Runt domain). We fused the green fluorescent protein derivative Cerulean to the N-terminus of the Runt domain and the green fluorescent protein derivative Venus to the N-terminus of CBFβ-SMMHC (as well as to CBFβ (Gorczynski, Grembecka et al. 2007)). The ratio of the emission intensities at 525 nm and 474 nm, measured after excitation at 433 nm, was used as the readout in this assay. The dynamic range for the FRET assay was determined by adding a 30-fold excess of untagged CBFβ-SMMHC (or CBFβ in the case of CBFβ-Runt domain binding) to the assay and the associated change in the FRET ratio was defined as 100% inhibition. We have validated the CBFβ-SMMHC-Runt domain assay by determining the $K_d$ for binding using serial dilution resulting in a $K_d$ value of 15 nM, in good agreement with the $K_d$ value of 6 nM obtained from calorimetric measurements of the binding of unmodified Runt domain to unmodified CBFβ-SMMHC (Lukasik, Zhang et al. 2002).

TR-FRET Assay.

It is essential to have a secondary assay to rule out false positives resulting from interference with the primary assays we conduct. To that end, we have also developed a TR-FRET (Time Resolved FRET) assay for these interactions. Due to time resolved detection, this approach has the distinct advantage of being substantially less sensitive to autofluorescence of small molecules and is therefore quite effective at identifying false positives arising from such effects (Bazin, Preaudat et al. 2001; Imbert, Unterreiner et al. 2007). We are using His-tagged Runt domain, a Tb-labeled anti-his tag antibody (donor), and Venus-CBFβ-SMMHC (acceptor) for the TR-FRET assay. Excitation is performed at 337 nm (Tb) and the emission is read out at 490 nm (Tb) and 520 nm (Venus-CBFβ-SMMC). Binding of the two proteins results in an increase in the 520/490 emission ratio whereas disruption of this interaction results in a decrease in the 520/490 emission ratio. Because of the long lifetime of the Tb fluorescence, acquisition of the emission signal can be delayed by several hundred microseconds after excitation, resulting in the substantial decay of fluorescence derived from small molecules. This will eliminate much of the fluorescent interference from small molecules, thus identifying false positives arising from such fluorescence effects. The TR-FRET assay was validated by running the titration experiment with unlabeled CBFβ-SMMHC protein which was competing with Venus-CBFβ-SMMHC for binding to the Runt domain. This resulted in an $IC_{50}$ value of 200 nM, in good agreement with the value obtained by FRET ($IC_{50}$=47 nM; the difference results from the 3-fold higher protein concentration used in TR-FRET in order to obtain an adequate dynamic range for the TR-FRET assay).

Controls for Promiscuous Inhibition by Micelle Formation or Covalent Binding.

As shown by Shoichet and co-workers (Seidler, McGovern et al. 2003), a primary source of false positives in any screen is micelle formation. In order to test for this, all active compounds are screened a second time by FRET in the presence of Triton detergent (Feng and Shoichet 2006). A substantial loss of activity in the presence of detergent is a hallmark of inhibition by micelle formation and such compounds are thus identified as false positives. In addition, we are also incubating compound with protein and checking by mass spectroscopy to ensure that positive hits are not acting by covalent addition to either of the proteins.

NMR Spectroscopy for Validation of Lead Compounds.

Validation of binding of a small molecule inhibitor to its protein target is an essential step in developing potent inhibitors. This can be readily achieved using either NMR spectroscopy or X-ray crystallography. In the case of X-ray crystallography, this is achieved by co-crystallization of the protein with the ligand and determination of the structure. In the case of NMR spectroscopy, the structure of a compound-protein complex can also be determined. In addition, chemical shift perturbations of the protein NMR spectrum (typically 2D $^{15}$N-$^{1}$H HSQC or $^{13}$C-$^{1}$H HSQC) in the presence of compounds can both confirm binding to the target and localize the binding site on a protein (Pellecchia, Sem et al. 2002; Salvatella and Giralt 2003). The latter method is a quick and efficient method to confirm binding to the protein and to determine the binding site when appropriate labeled samples are available and the resonance assignments are known. Such data can also be used to dock the small molecule to the protein. Because the structure of CBFβ has been solved by NMR (Huang, Peng et al. 1999), resonance assignments are available and we have employed this approach as an additional screen to ensure the validity of the inhibitors we are developing and to determine the binding site (see below).

Development of Aminothiazole Inhibitors—Identification of Allosteric Site on CBFβ.

Using a combination of virtual screening, FRET assays, and NMR we previously identified a 2-amino-thiazole class of inhibitors of the binding of the Runt domain to CBFβ (Gorczynski, Grembecka et al. 2007). These were optimized to low micromolar inhibitors of the CBFβ-Runt domain interaction. The most potent compounds were subsequently shown to inhibit the growth of inv(16) cell lines and induce changes in morphology consistent with increased differentiation. Using NMR, we showed that these compounds do not bind to the Runt domain heterodimerization interface on CBFβ but rather to an allosteric site on the other side of the protein. However, subtle chemical shift changes were also observed for residues at the binding interface, consistent with a subtle alteration of the structure or dynamics at the interface mediating inhibition. Strikingly, all subsequent screening efforts to identify new leads have resulted in identification only of compounds which bind to this allosteric site, not the heterodimerization interface, suggesting the latter is a difficult target for small molecule binding.

While this class of compounds clearly provided proof-of-principle, we have identified herein a benzimidazole lead which is already more potent in inhibiting CBFβ-SMMHC binding to the Runt domain than the best optimized 2-aminothiazole in vitro and shows superior effects against inv (16) cell lines (see below). The benzimidazole class also shows improved solubility properties relative to the aminothiazoles. For these reasons, we are currently pursuing further development of the benzimidazole class rather than the aminothiazoles.

Screen of NCI Compound Library.

We used the FRET assay described above to screen the NCI Diversity Set (1990 compounds). Positive hits from this screen were subsequently checked by NMR for chemical shift perturbations in $15N$-$^1H$ HSQC spectra, as described above. This resulted in the identification of one lead compound. This compound, NCI 320656, showed an $IC_{50}$ of 16 µM for inhibition of CBF-SMMHC/Runt domain binding (see Table 1 below; AI-4-57=NCI 320656). This is roughly the same, without any optimization, to the ~10 µM $IC_{50}$ we observe for the optimized 2-aminothiazole inhibitors for the inhibition of the CBF-SMMHC/Runt domain interaction. With optimization, we should be able to create substantially more potent inhibitors starting from this lead. Importantly, data on the NCI Developmental Therapeutics website indicate that this compound is tolerated by mice at concentrations up to 200 mg/kg/day via ip injection. In addition, the data for inhibition of the NCI 60 cell lines shows that for 79% of the cell lines the $GI_{50}$ is ≥100 µM, indicating a lack of general cytotoxicity.

Table 1 summarizes some of the monomer benzimidazoles used herein and provides structures and biologic activity of the tested compounds. Note that some of the compounds described herein have more than one name and each name is provided herein.

TABLE 1

Activity of Benzimidazole inhibitors

| Compound | Structure | NMR with CBFβ+ 250 µM compound G 112/K 98 | $IC_{50}$FRET (µM) (CBFβ-SMMHC: RD, 20 nM both) | Δ (%) |
|---|---|---|---|---|
| NCI-320656 | 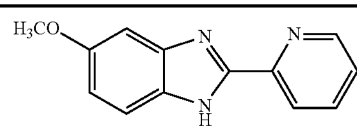 | CSP 0.039/0.026 ppm | 16 | 85 |
| AI-4-57 (or) LD-1-11C | 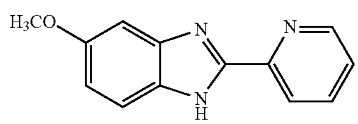 [SMILES: COc1ccc2[nH]c(-c3ccccn3)nc2c1] | CSP 0.039/0.026 ppm | 2.6 | 46 |
| AI-4-52 | 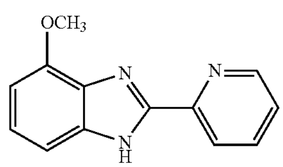 [SMILES: COc1cccc2[nH]c(-c3ccccn3)nc12] | | 5.5 | 39 |
| LD-1-29 (or) AI-10-54 | 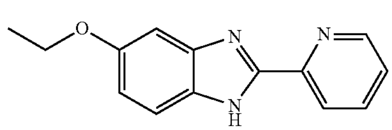 [SMILES: CCOc1ccc2[nH]c(-c3ccccn3)nc2c1] | CSP 0.026/no change ppm | 1.5 | 44 |

TABLE 1-continued

Activity of Benzimidazole inhibitors

| Compound | Structure | NMR with CBFβ+ 250 μM compound G 112/K 98 | IC$_{50}$FRET (μM) (CBFβ-SMMHC: RD, 20 nM both) | Δ (%) |
|---|---|---|---|---|
| AI-4-42 | 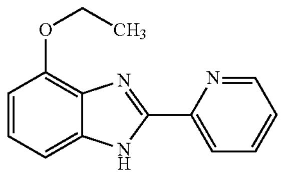 [SMILES: CCOc1cccc2[nH]c(-c3ccccn3)nc12] | | 4.2 | 38 |
| AI-4-70 (or) LD-2-21 | 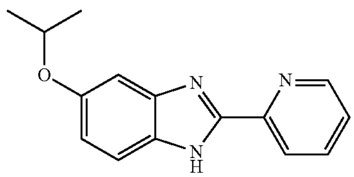 [SMILES: CC(C)Oc1ccc2[nH]c(-c3ccccn3)nc2c1] | No CSP | 1.4 | 40 |
| LD-1-127 | 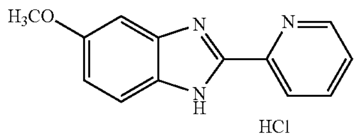 [SMILES: COc1ccc2[nH]c(-c3ccccn3)nc2c1 ; Cl] | | 2 | 53 |
| AI-10-61 | 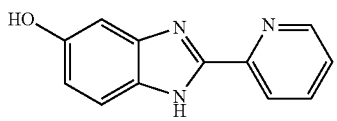 [SMILES: Oc1ccc2[nH]c(-c3ccccn3)nc2c1] | No CSP | 2.5 | 33 |
| LD-1-138 | 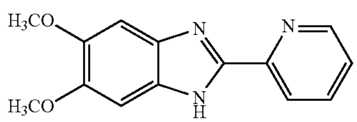 [SMILES: COc1cc2nc(-c3ccccn3)[nH]c2cc1OC] | | 4.6 | 41 |
| AI-10-35 | 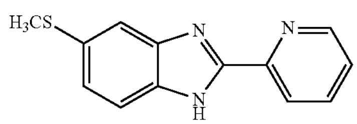 | CSP 0.037/0.027 ppm | 1.8 | 47 |
| AI-10-37 | 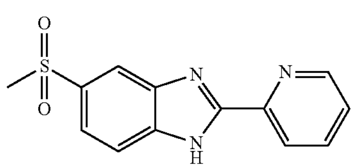 [SMILES: CS(=O)(=O)c1ccc2[nH]c(-c3ccccn3)nc2c1] | | 3.3 | 53 |
| AI-10-47 | 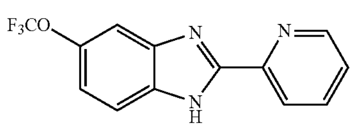 [SMILES: FC(F)(F)Oc1ccc2[nH]c(-c3ccccn3)nc2c1] | No CSP (some precipitation) | 1.0 | 43 |
| LD-2-11 | 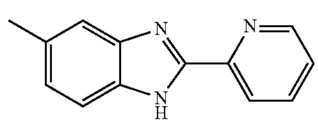 [SMILES: Cc1ccc2[nH]c(-c3ccccn3)nc2c1] | | 2.9 | 29 |
| AI-4-46 | 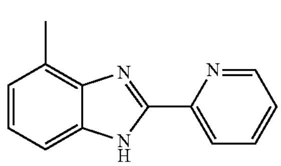 [SMILES: Cc1cccc2[nH]c(-c3ccccn3)nc12] | | 5.3 | 35 |

TABLE 1-continued

Activity of Benzimidazole inhibitors

| Compound | Structure | NMR with CBFβ+ 250 μM compound G 112/K 98 | IC$_{50}$FRET (μM) (CBFβ-SMMHC: RD, 20 nM both) | Δ (%) |
|---|---|---|---|---|
| LD-1-23 | 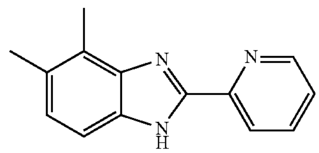 [SMILES: Cc1ccc2[nH]c(-c3ccccn3)nc2c1C] | No CSP (some precipitation) | 4.3 | 56 |
| LD-1-37 | 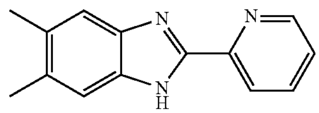 [SMILES: Cc1cc2nc(-c3ccccn3)[nH]c2cc1C] | | 2 | 31 |
| LD-1-31 | 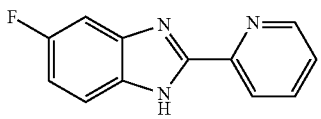 [SMILES: Fc1ccc2[nH]c(-c3ccccn3)nc2c1] | No CSP Strong precipitation) | 2.5 | 35 |
| LD-1-33 | 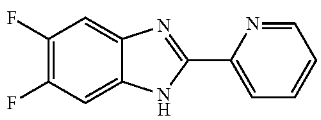 [SMILES: Fc1cc2nc(-c3ccccn3)[nH]c2cc1F] | | 2.5 | 26 |
| AI-4-43 | 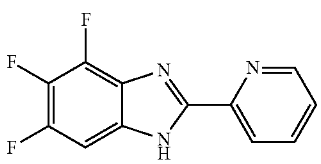 [SMILES: Fc1cc2[nH]c(-c3ccccn3)nc2c(F)c1F] | | 1.4 | 41 |
| LD-1-39 | 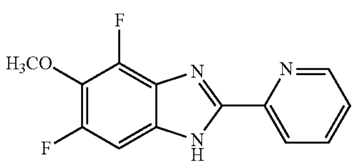 [SMILES: COc1c(F)cc2[nH]c(-c3ccccn3)nc2c1F] | No CSP | 1.3 | 31 |
| LD-2-79 | 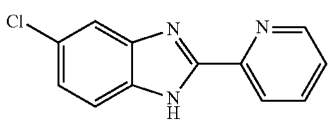 [SMILES: Clc1ccc2[nH]c(-c3ccccn3)nc2c1] | | 2.3 | 42 |
| AI-10-51 | 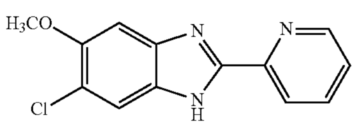 [SMILES: COc1cc2nc(-c3ccccn3)[nH]c2cc1Cl] | | 1.3 | 39 |
| AI-4-49 | 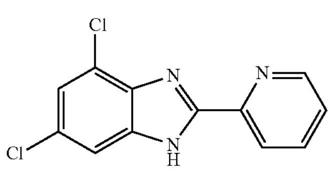 [SMILES: Clc1cc(Cl)c2nc(-c3ccccn3)[nH]c2c1] | | 0.7 | 49 |
| LD-2-23 | 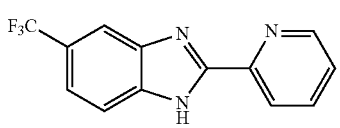 [SMILES: FC(F)(F)c1ccc2[nH]c(-c3ccccn3)nc2c1] | | 1.1 | 30 |

TABLE 1-continued
Activity of Benzimidazole inhibitors
| Compound | Structure | NMR with CBFβ+ 250 μM compound G 112/K 98 | IC$_{50}$FRET (μM) (CBFβ-SMMHC: RD, 20 nM both) | Δ (%) |
|---|---|---|---|---|
| AI-4-47 | 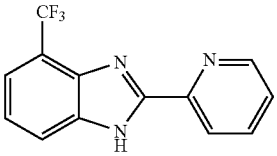 [SMILES: FC(F)(F)c1cccc2[nH]c(-c3ccccn3)nc12] | | Interference with assay | |
| AI-4-48 | 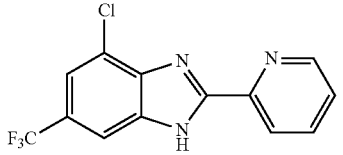 [SMILES: FC(F)(F)c1cc(Cl)c2nc(-c3ccccn3)[nH]c2c1] | | 0.76 | 49 |
| LD-2-63 | 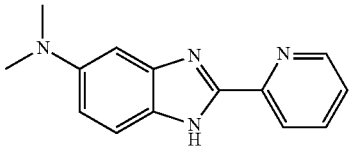 [SMILES: CN(C)c1ccc2[nH]c(-c3ccccn3)nc2c1] | CSP 0.037/0.023 ppm | Interference with assay | |
| AI-10-83 | 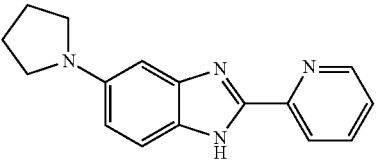 [SMILES: c1ccc(-c2nc3cc(N4CCCC4)ccc3[nH]2)nc1] | Big CSP 0.087/0.039 ppm L 97 = 0.034 ppm | Interference with assay | |
| AI-10-82 | 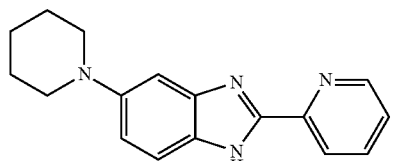 | CSP 0.032/0.016 ppm | Interference with assay | |
| AI-10-3 | 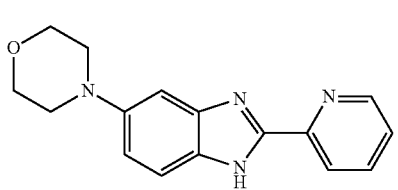 [SMILES: c1ccc(-c2nc3cc(N4CCOCC4)ccc3[nH]2)nc1] | No CSP | 1.0 | 31 |
| AI-10-88 | 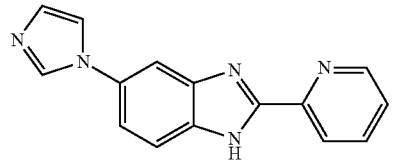 [SMILES: c1ccc(-c2nc3cc(-n4ccnc4)ccc3[nH]2)nc1] | No CSP | 3.4 | 53 |
| AI-10-57 | 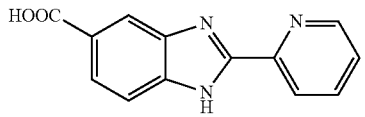 [SMILES: O=C(O)c1ccc2[nH]c(-c3ccccn3)nc2c1] | No CSP | 40 | 67 |
| AI-10-70 | 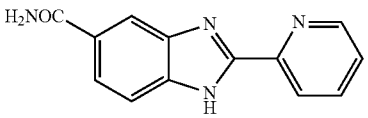 | | NS | Δ$_{500}$ = 60 |

TABLE 1-continued

Activity of Benzimidazole inhibitors

| Compound | Structure | NMR with CBFβ+ 250 μM compound G 112/K 98 | IC$_{50}$FRET (μM) (CBFβ-SMMHC: RD, 20 nM both) | Δ (%) |
|---|---|---|---|---|
| AI-10-97 | 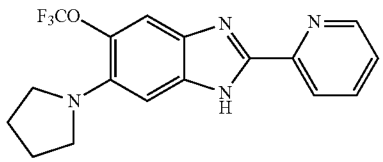 [SMILES: FC(F)(F)Oc1cc2nc(-c3ccccn3)[nH]c2cc1N1CCCC1] | CSP 0.012/0.006 ppm | Interference with assay | |
| AI-10-96 | 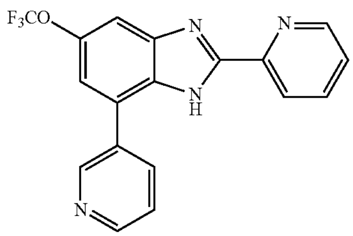 [SMILES: FC(F)(F)Oc1cc(-c2cccnc2)c2[nH]c(-c3ccccn3)nc2c1] | No CSP | 2.0 | 31 |
| AI-4-61 (or) AI-10-52 | 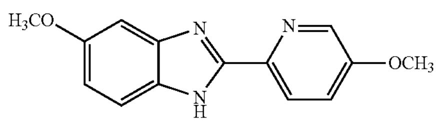 [SMILES: COc1ccc(-c2nc3cc(OC)ccc3[nH]2)nc1] | CSP 0.015/0.013 ppm | 2.5 | 34 |
| AI-10-101 | 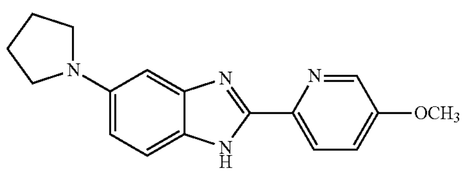 [SMILES: COc1ccc(-c2nc3cc(N4CCCC4)ccc3[nH]2)nc1] | | Interference with assay | |
| AI-10-11 | 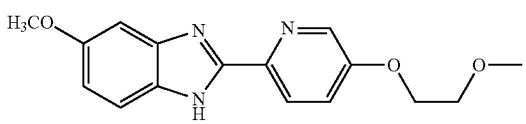 [SMILES: COCCOc1ccc(-c2nc3cc(OC)ccc3[nH]2)nc1] | | 2.3 | 34 |
| AI-10-87 | 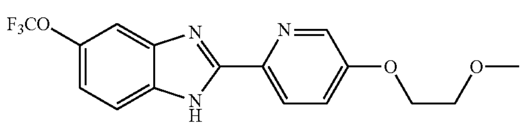 [SMILES: COCCOc1ccc(-c2nc3cc(OC(F)(F)F)ccc3[nH]2)nc1] | | 2.3 | 37 |
| AI-10-53 | 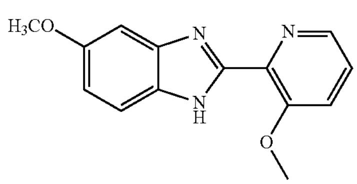 [SMILES: COc1ccc2[nH]c(-c3ncccc3OC)nc2c1] | CSP 0.028/0.02 ppm | 3.0 | 61 |
| AI-10-69 | 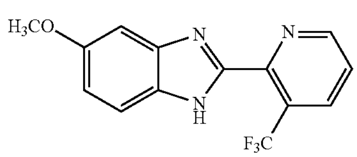 [SMILES: COc1ccc2[nH]c(-c3ncccc3C(F)(F)F)nc2c1] | | NW | $\Delta_{167}$ = 18 |
| AI-10-63 | 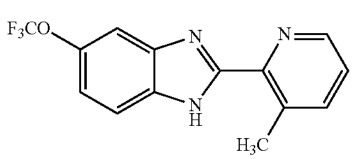 [SMILES: Cc1cccnc1-c1nc2cc(OC(F)(F)F)ccc2[nH]1] | | NS | $\Delta_{500}$ = 61 |

TABLE 1-continued

Activity of Benzimidazole inhibitors

| Compound | Structure | NMR with CBFβ+ 250 μM compound G 112/K 98 | IC$_{50}$FRET (μM) (CBFβ-SMMHC: RD, 20 nM both) | Δ (%) |
|---|---|---|---|---|
| AI-10-65 | 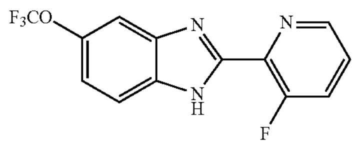 [SMILES: Fc1cccnc1-c1nc2cc(OC(F)(F)F)ccc2[nH]1] | | 22 | 53 |
| AI-10-64 | 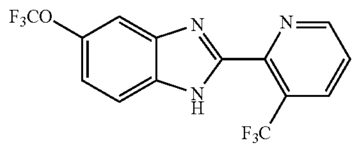 [SMILES: FC(F)(F)Oc1ccc2[nH]c(-c3ncccc3C(F)(F)F)nc2c1] | | NS | Δ$_{500}$ = 50 |
| LD-2-101 | 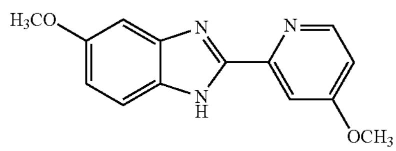 [SMILES: COc1ccnc(-c2nc3cc(OC)ccc3[nH]2)c1] | No CSP | 1.0 | 47 |
| AI-10-77 | 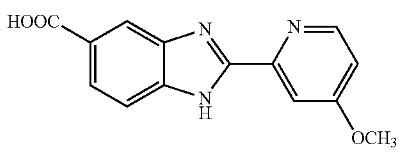 [SMILES: COc1ccnc(-c2nc3cc(C(=O)O)ccc3[nH]2)c1] | | 2.0 | 21 |
| LD-2-91 | 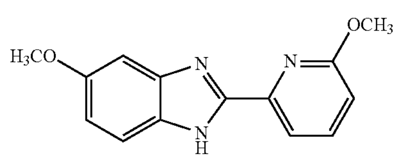 [SMILES: COc1ccc2[nH]c(-c3cccc(OC)n3)nc2c1] | | NA | |
| AI-4-55 | 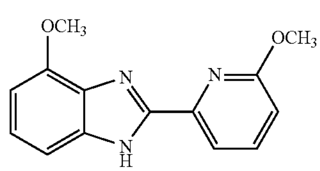 [SMILES: COc1cccc(-c2nc3c(OC)cccc3[nH]2)n1] | | NA | |
| LD-2-89 | 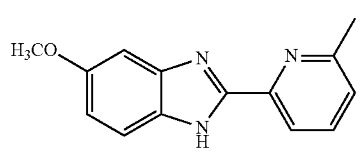 [SMILES: COc1ccc2[nH]c(-c3cccc(C)n3)nc2c1] | | NS | Δ$_{333}$ = 17 |
| LD-2-99 | 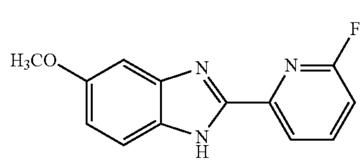 [SMILES: COc1ccc2[nH]c(-c3cccc(F)n3)nc2c1] | | NA | |
| LD-1-75 | 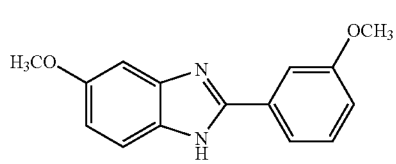 [SMILES: COc1cccc(-c2nc3cc(OC)ccc3[nH]2)c1] | | NA | |

TABLE 1-continued

Activity of Benzimidazole inhibitors

| Compound | Structure | NMR with CBFβ+ 250 μM compound G 112/K 98 | IC$_{50}$FRET (μM) (CBFβ-SMMHC: RD, 20 nM both) | Δ (%) |
|---|---|---|---|---|
| AI-4-53 | 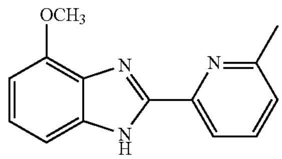 [SMILES: COc1cccc2[nH]c(-c3cccc(C)n3)nc12] | | NA | |
| AI-4-55 | 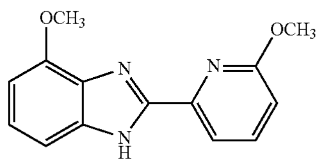 [SMILES: COc1cccc(-c2nc3c(OC)cccc3[nH]2)n1] | | NA | |
| LD-1-73 | 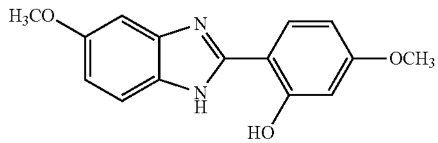 [SMILES: COc1ccc(-c2nc3cc(OC)ccc3[nH]2)c(O)c1] | | NS | Δ$_{110}$ = 30 |
| AI-4-44 | 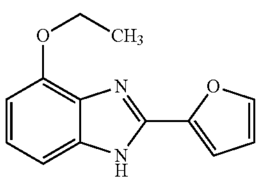 [SMILES: CCOc1cccc2[nH]c(-c3ccco3)nc12] | | NA | |
| AI-4-45 | 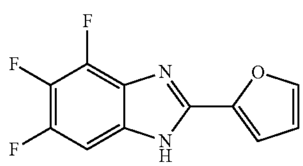 [SMILES: Fc1cc2[nH]c(-c3ccco3)nc2c(F)c1F] | | NA | |

Of the above-identified monomers, the following are novel and being disclosed herein: AI-4-70 (LD-2-21), LD-1-138, AI-10-35, AI-10-37, AI-10-47, LD-1-33, AI-4-43, LD-1-39, AI-10-51, AI-4-49, AI-4-48, AI-10-83, AI-10-82, AI-10-3, AI-10-70, AI-10-97, AI-10-96, AI-4-61 (AI-10-52), AI-10-101, AI-10-11, AI-10-87, AI-10-53, AI-10-69, AI-10-63, AI-10-65, AI-10-64, LD-2-101, AI-10-77, LD-2-91, AI-4-55, LD-2-99, LD-1-75, AI-4-53, AI-4-55, LD-1-73, AI-4-44, and AI-4-45.

Elaboration of Benzimidazole Class.

Figure 2:
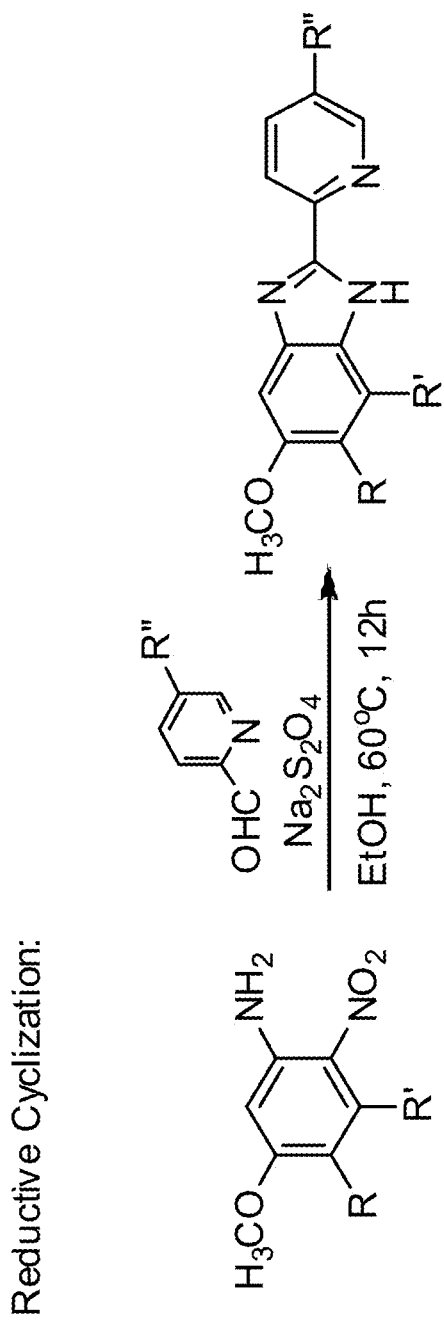
FIG. 2. Synthetic scheme used to prepare AI-4-57 (NCI320656) (R=R', R"=H).

The best benzimidazole class compound to emerge from the screening efforts described herein is NCI 320656, from the NCI Diversity Set. We have synthesized this compound (internal name: AI-4-57) using the synthetic route shown in FIG. 2, confirmed its activity by FRET, and confirmed binding to CBFβ by NMR spectroscopy. Please note that the structure shown in FIG. 2 is a regioisomer (5-methoxy versus 4-methoxy) of the structure listed on the NCI Diversity Set webpage, as we showed by synthesis of both isomers and comparison of the NMR data to that of the compound provided by NCI that the 5-methoxy isomer is the actual compound in the library. Using a similar synthetic route, analogs have been prepared and assayed to probe the structure-activity relationships (SAR) and assess sites where we can introduce a linker for dimer formation (see below). All compounds are being fully characterized by $^1$H NMR, $^{13}$C NMR, mass spec, and combustion analysis prior to biological testing. Table 1 lists IC$_{50}$ data for a number of active compounds of the invention.

Modeling of Benzimidazole Binding to CBFβ.

Figure 3:
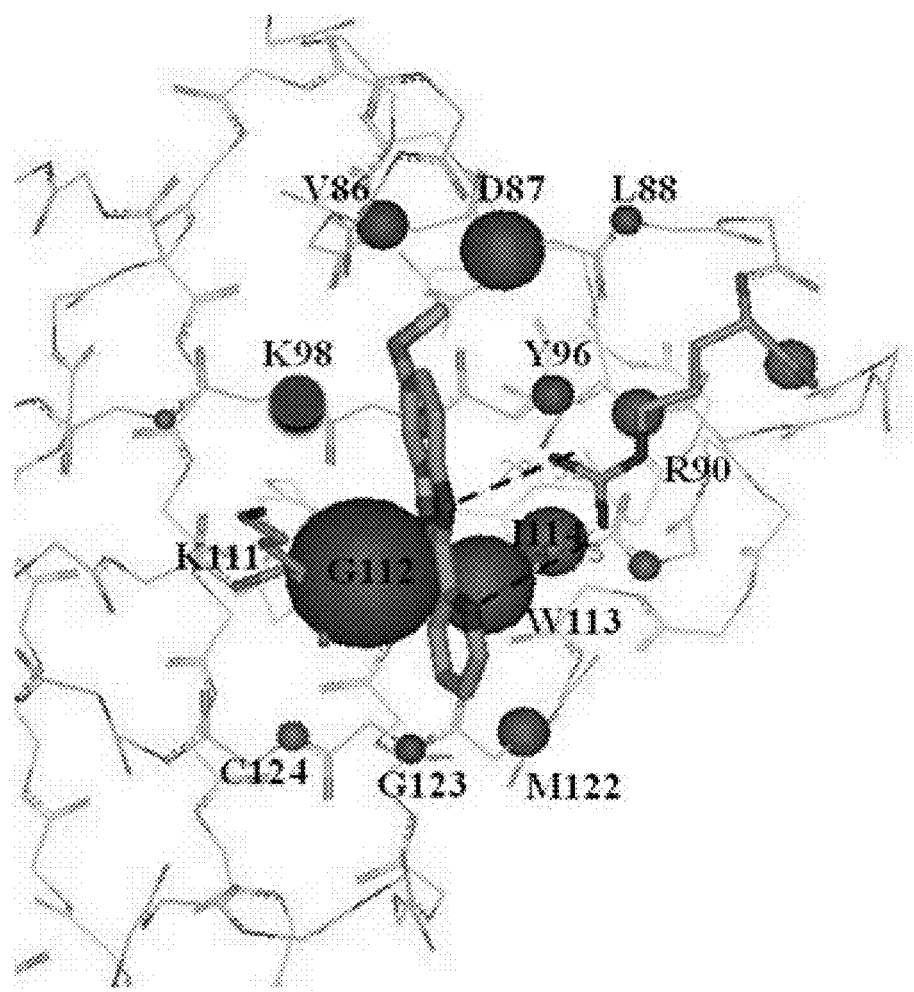
FIG. 3. Binding mode for AI-4-57 on the structure of CBFβ. Blue and red balls indicate NH chemical shift changes in CBFβ upon binding. The size of the ball is proportional to the magnitude of the chemical shift change.

As seen for the amino-thiazole inhibitors NMR chemical shift changes upon addition of compound to CBFβ clearly show that the NCI library compound binds in the allosteric site we previously identified. Based on the localization of the binding site from NMR data, the program GLIDE (Friesner, Banks et al. 2004; Halgren, Murphy et al. 2004; Friesner, Murphy et al. 2006) was used to dock NCI320656 (AI-4-57) to CBFβ. This resulted in two possible orientations for the compound in the binding site. In order to distinguish these two possible orientations, an analog has been synthesized with an ethyl group at the 5-position of the pyridine ring system. One of the docking models predicts a steric clash for this substituent whereas the other does not. FRET measurement of the activity yields an IC$_{50}$ value of 2 μM, i.e., it has similar activity to the parent compound, which is consistent with only one of the two models (see FIG. 3). The availability of this docking model will make it possible to design substitutions on the parent compound and predict their efficacy using GLIDE, making for a more efficient approach to optimize this class of compounds.

Effects on Inv(16) Cell Lines.

Figure 4:
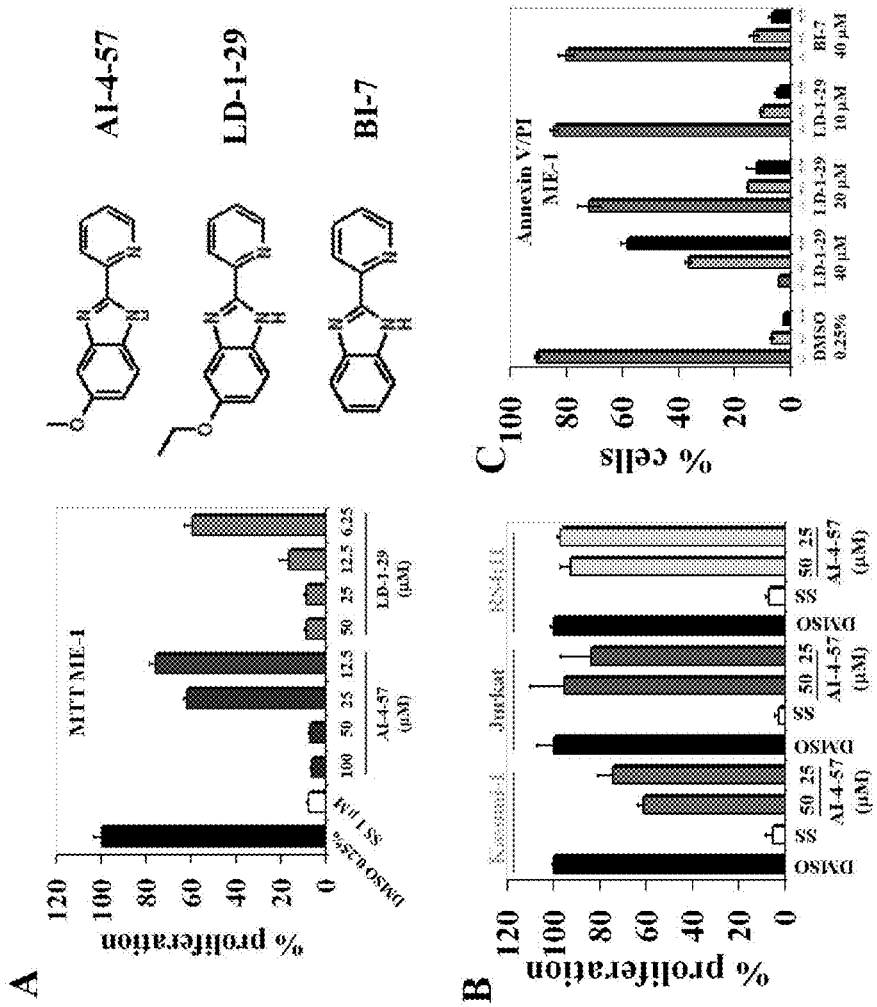
FIG. 4. Structures of two active (AI-4-57 and LD-1-29) and one inactive compound (BI-7). 4A. Growth inhibition of ME-1 cells measured by MTT assay for AI-4-57 and LD-1-29. 4B. Growth inhibition of Kasumi-1, Jurkat, and RS4;11 cells with AI-4-57 measured by MTT assay. 4C. Percentages of cells that are AnnexinV/PI (−/−) (green), AnnexinV/PI (+/−) (grey), and AnnexinV/PI (+/+) (black) for LD-1-29 and BI-7.

We have tested several of the compounds we have synthesized for their effects on ME-1 cells, a leukemia cell line harboring the inv(16) (Yanagisawa, Horiuchi et al. 1991). Two active compounds (AI-4-57 FRET $IC_{50}$=1.3 µM and LD-1-29 FRET $IC_{50}$=0.7 µM) and one inactive compound (BI-7 FRET $IC_{50}$=>250 µM) have been employed for these studies. Effects on growth have been assayed using an MTT viability assay (Mosmann 1983) for the 2 active compounds (see FIG. 4.A), showing effective inhibition of growth by these 2 compounds. AI-4-57 has also been tested against the Kasumi-1, Jurkat, and RS4;11 leukemia cell lines (FIG. 4.B). No effect on growth was seen for the Jurkat and RS4;11 cell lines, non-CBF leukemia cell lines, whereas there was a modest effect on Kasumi-1 cells, a CBF leukemia cell line (harbors the AML1-ETO fusion). We have also examined effects on apoptosis using flow cytometry to measure Annexin V/PI (propidium iodide) positivity. FIG. 4.C shows a bar graph of effects of 3 different concentrations of LD-1-29 and one concentration of BI-7 on the percentages of cells which are AnnexinV/PI (−/−) (non-apoptotic cells), AnnexinV/PI (+/−) (early apoptotic cells), and AnnexinV/PI (+/+) (late apoptotic cells). There is a clear dose-dependent increase in the percentage of apoptotic cells with LD-1-29 whereas BI-7 shows little to no effect at the 40 µM concentration where LD-1-29 shows substantial apoptosis. The selectivity for specific cell lines and the correlation of activity in the FRET assay with effects on inv(16) cells all support the hypothesis that the compounds are hitting the desired target.

Rationale for Increased Specificity by Use of Dimeric Inhibitors.

Numerous studies have demonstrated that cancer cells are frequently "addicted", or highly dependent upon, specific oncogenes (Sharma and Settleman 2007; Weinstein and Joe 2008). One clear example of this is found in chronic myeloid leukemia (CML) where the BCR-ABL fusion protein found in these cells is essential. Inhibition of this activated kinase with imatinib (Gleevec) has proven extraordinarily effective in treating these patients (Druker 2004; Lydon and Druker 2004). Similarly, it is our hypothesis that the inhibition of CBFβ-SMMHC is likely to be effective for inv(16) leukemia. In CML, imatinib inhibits the activity of BCR-ABL as well as the remaining wildtype ABL present in cells, yet the leukemia cells are effectively eliminated because of the addiction of these cells to BCR-ABL. Based on this analogy, it is plausible that small molecule inhibitors targeting CBFβ, thereby affecting both CBFβ-SMMHC as well as wildtype CBFβ, may be effective and are worth pursuing.

However, a recent study where the dosage of CBFβ was reduced in the presence of CBFβ-SMMHC in a mouse model showed enhanced leukemogenesis, suggesting that inhibition of both CBFβ and CBFβ-SMMHC may not be effective. Therefore, it is also important to develop inhibitors that can selectively inhibit CBFβ-SMMHC with minimal effects on CBFβ. In order to achieve this, we are proposing to take advantage of the oligomeric nature of CBFβ-SMMHC and apply the principles of poly-valency (Mammen, Choi et al. 1998; Kiessling, Gestwicki et al. 2006) to achieve the desired selectivity. Consistent with existing literature on myosin, we have shown that truncated forms of CBFβ-SMMHC lacking the extreme C-terminus form dimers in solution (Lukasik, Zhang et al. 2002). For the full-length protein, these dimers then oligomerize to form high order oligomers (Shigesada, van de Sluis et al. 2004). In contrast, CBFβ is monomeric in solution. This difference in oligomerization provides a means to achieve selective inhibition of CBFβ-SMMHC versus CBFβ.

Figure 5:
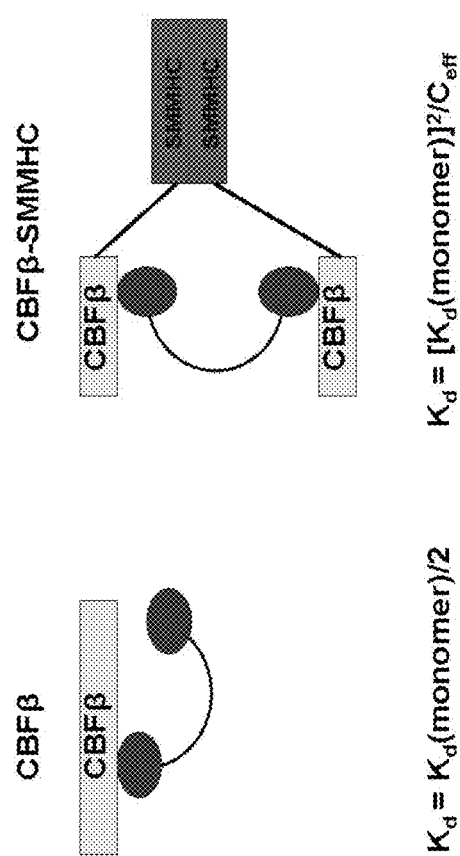
FIG. 5. Schematic representation of the binding enhancement achieved by means of a bi-valent CBFβ-SMMHC-ligand interaction versus a mono-valent CBFβ-ligand interaction.

As shown in FIG. 5, the dissociation constant for a monovalent compound binding to monomeric CBFβ is equal to $K_d$(monomer). If we create a homo-dimer of this compound, it will bind the monomeric CBFβ protein with a dissociation constant equal to $K_d$(monomer)/2. However, this same homo-dimer will interact with two sites on the dimeric CBFβ-SMMHC protein and have a $K_d$(dimer) equal to $(K_d(monomer))^2/C_{eff}$ where $C_{eff}$ is the effective concentration resulting from the tethering of the two binding sites on CBFβ-SMMHC to one another (Mulder, Auletta et al. 2004). Recent analysis of the dependence of $C_{eff}$ values in proteins based on the intervening length of flexible peptide make it possible to accurately estimate $C_{eff}$ values (Goldenberg 2003). We have assigned the NMR resonances of a CBFβ-SMMHC construct and measured heteronuclear NOE to establish the length of the flexible region between CBFβ and the myosin coiled coil. Our knowledge of the linker length between the CBFβ and myosin coiled coil makes it possible to estimate $C_{eff}$, resulting in a predicted value of $6$-$40*10^{-3}$ M (there are two different models for $C_{eff}$ calculations and most experimental values fall between these two models). Thus, a monomer with a $K_d$ of 10 µM, when appropriately tethered, will yield an inhibitor with a predicted $K_d$ as low as 2.5-17 nM, neglecting entropic losses necessary for binding. This corresponds to ~1000-fold selectivity for CBFβ-SMMHC. Without wishing to be bound by any particular theory, it is hypothesized herein that the creation of homo-dimers of CBFβ inhibitors will provide a means to achieve selectivity for CBFβ-SMMHC and thereby provide a mechanism to selectively inhibit CBFβ-SMMHC activity while minimally affecting CBFβ.

Synthesis of Dimeric Compounds.

Figure 6:
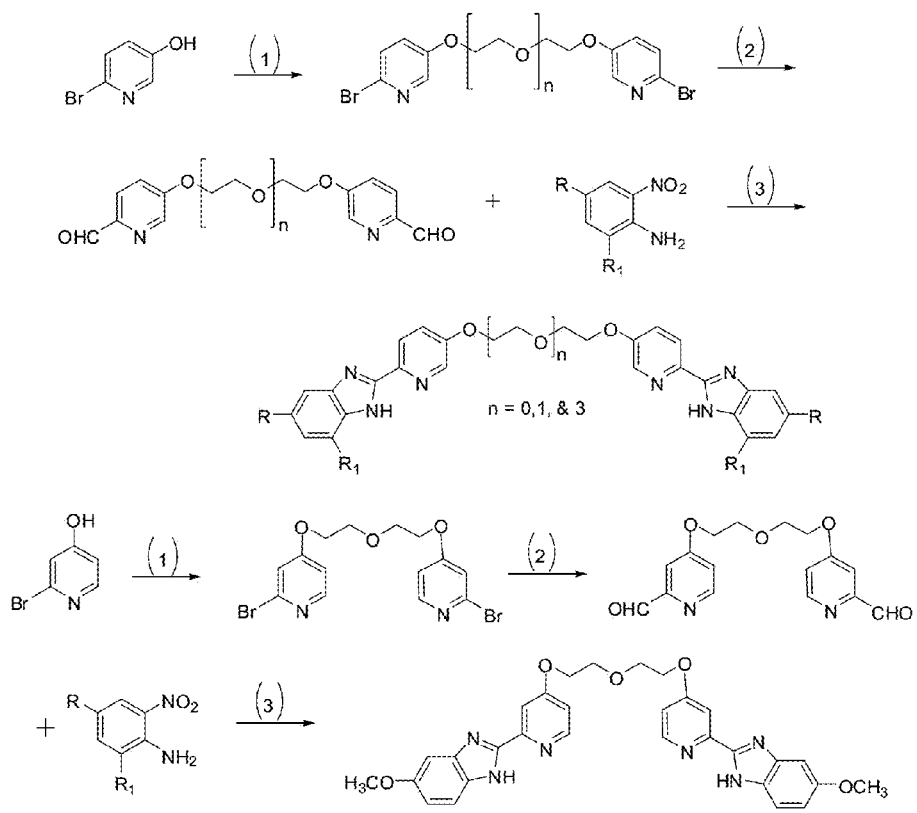
FIG. 6. Top: Synthetic route to dimers of benzimidazole inhibitors. Bottom: Structures of specific dimeric inhibitors.
Figure 6:

We are exploring linking of benzimidazole inhibitors via the pyridine ring with attachment at the 3, 4, and 5 positions of the pyridine ring. As shown in FIG. 6, we have developed an efficient approach to generate linked compounds through the 5 position. A series of differing length polyethylene glycol linkers have been incorporated (7, 10, 16 atoms). Testing of various linker lengths has shown the 7 atom linked compound to be the most potent so subsequent studies have focused on this compound (named AI-4-62 or AI-4-83 below).

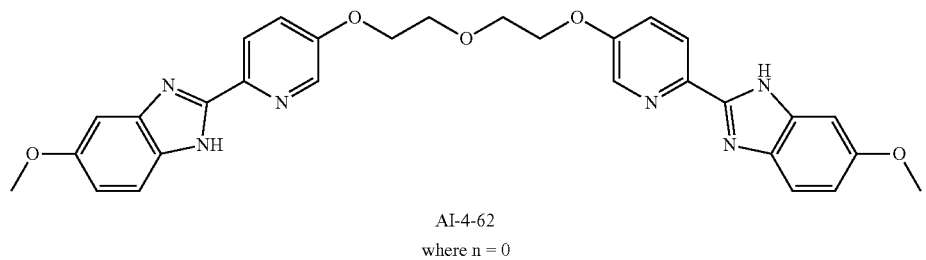

AI-4-62
where n = 0

Effects of Dimeric Compounds on ME-1 Cells (an Inv(16) Cell Line).

Figure 7:
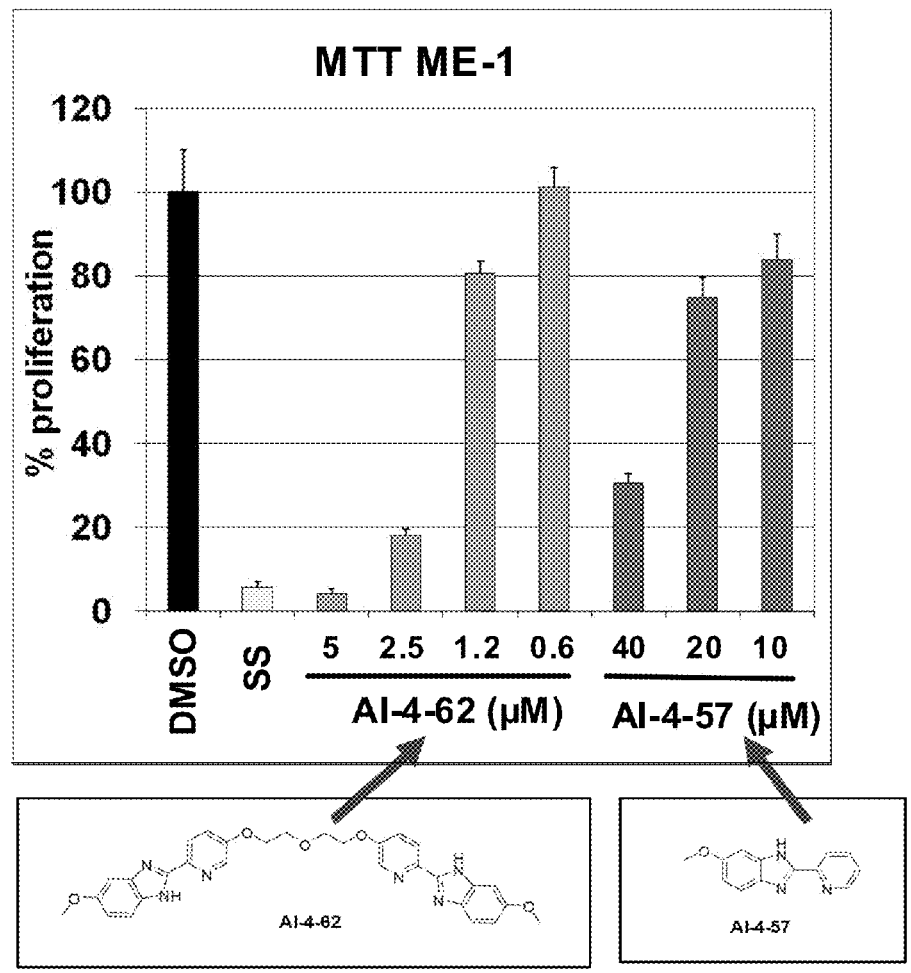
FIG. 7. Dose-dependent inhibition of ME-1 cell growth by monomer and dimer inhibitors measured by MTT assay. SS=staurosporine.

The dimer with a 7 atom linker (AI-4-62) has been tested for effects on the growth of the ME-1 cell line (see FIG. 7), a leukemia cell line with the inv(16). In order to demonstrate the efficacy of the dimer relative to the parent monomeric inhibitor, we have tested both on ME-1 cells. Strikingly, the dimeric compound is substantially (~15-fold) more potent than the corresponding monomer, indicating a substantial improvement in efficacy, as we predicted. These data and the in vitro assay results provide validation for the approach of developing dimeric inhibitors to enhance specificity as well as efficacy.

Effects of Dimeric Compounds on Other Leukemia Cell Lines.

Figure 8:
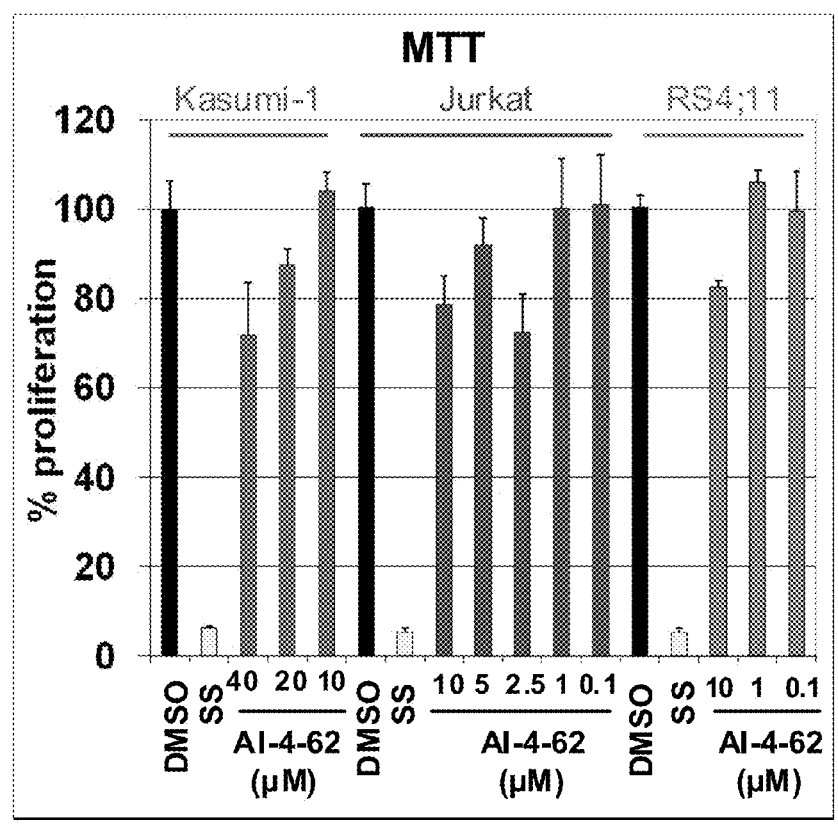
FIG. 8. Effects of AI-4-62 on growth of Kasumi-1, Jurkat, and RS4;11 cells.

In order to test the specificity of these compounds, we have tested the effect of AI-4-62 on several leukemia cell lines which do not have the inv(16): Kasumi-1 (AML with t(8;21)), Jurkat (ALL with complex cytogenetics), and RS4;11 (ALL with t(4;11)). As shown in FIG. 8, AI-4-62 had little to no effect on these cell lines at a concentration of 10 µM, a concentration where growth of ME-1 cells is 100% inhibited. This data provides strong evidence in support of the specificity of AI-4-62. Below are two exemplary dimeric compound formulas, shown here without the possible substituents indicated elsewhere herein.

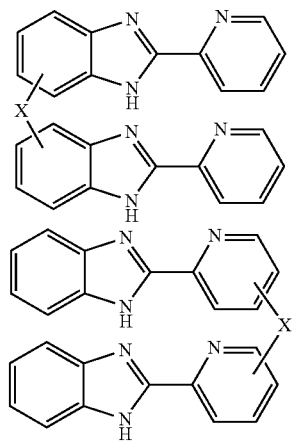

Effects of Dimeric Inhibitor on p21 Expression Level in ME-1 Cells.

Figure 9:
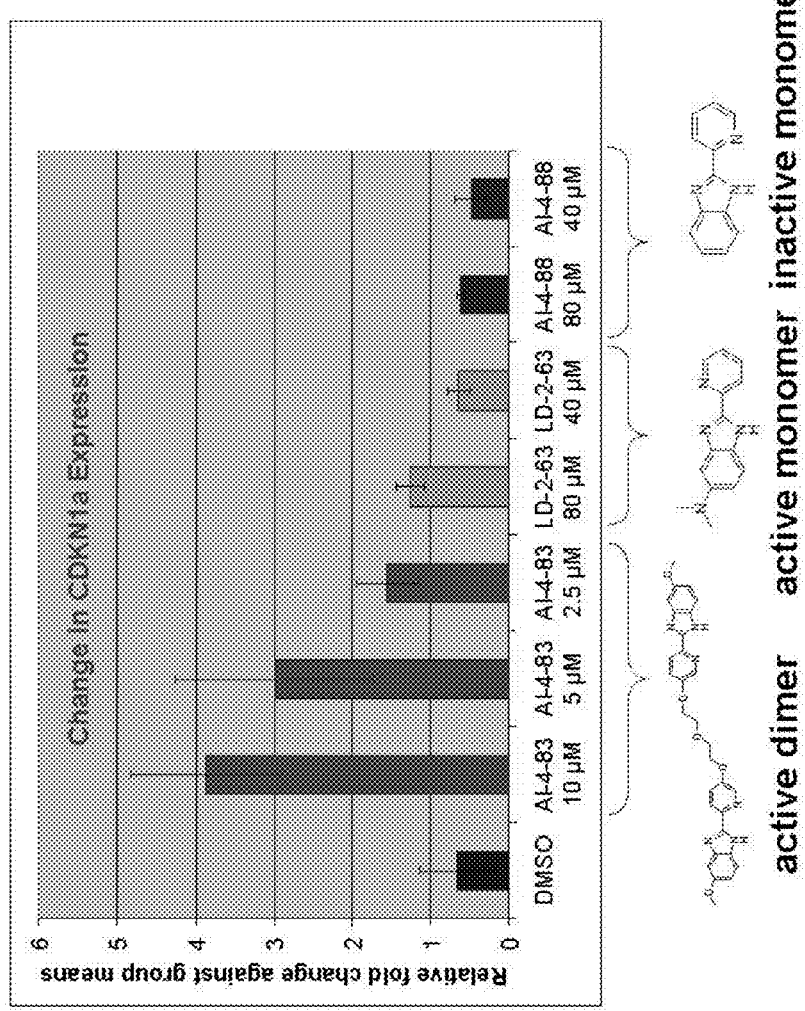
FIG. 9 depicts graphically the effects of: 1) AI-4-83; 2) an active monomer (LD-2-63); and 3) an inactive monomer (AI-4-88) on CDKN1α expression. The effects on CDKN1α expression were measured by RT-PCR. DMSO-control; AI-4-83 was used at 10, 5, and 2.5 μM; LD-2-63 was used at 80 and 40 μM; AI-4-88 was used at 80 and 40 μM.

The effects of the dimeric inhibitor AI-4-83 on CDKN1a gene expression were examined using RT-PCR. FIG. 9 shows a dose-dependent substantial increase in CDKN1a gene expression with AI-4-83 treatment which correlates well with the growth inhibitory effects of the compound.

This provides data showing a change in gene expression at a known RUNX target which has been shown to have its expression reduced by CBFβ-SMMHC, providing supporting data for the effect of the compound being direct. In addition, the effect of AI-4-83 is much more substantial than that for the monomeric compound, supporting the increased efficacy of the dimeric versus monomeric compounds.

Effects of Dimeric Inhibitor on Inv(16) Repression Using a Luciferase Reporter Assay.

Figure 10:
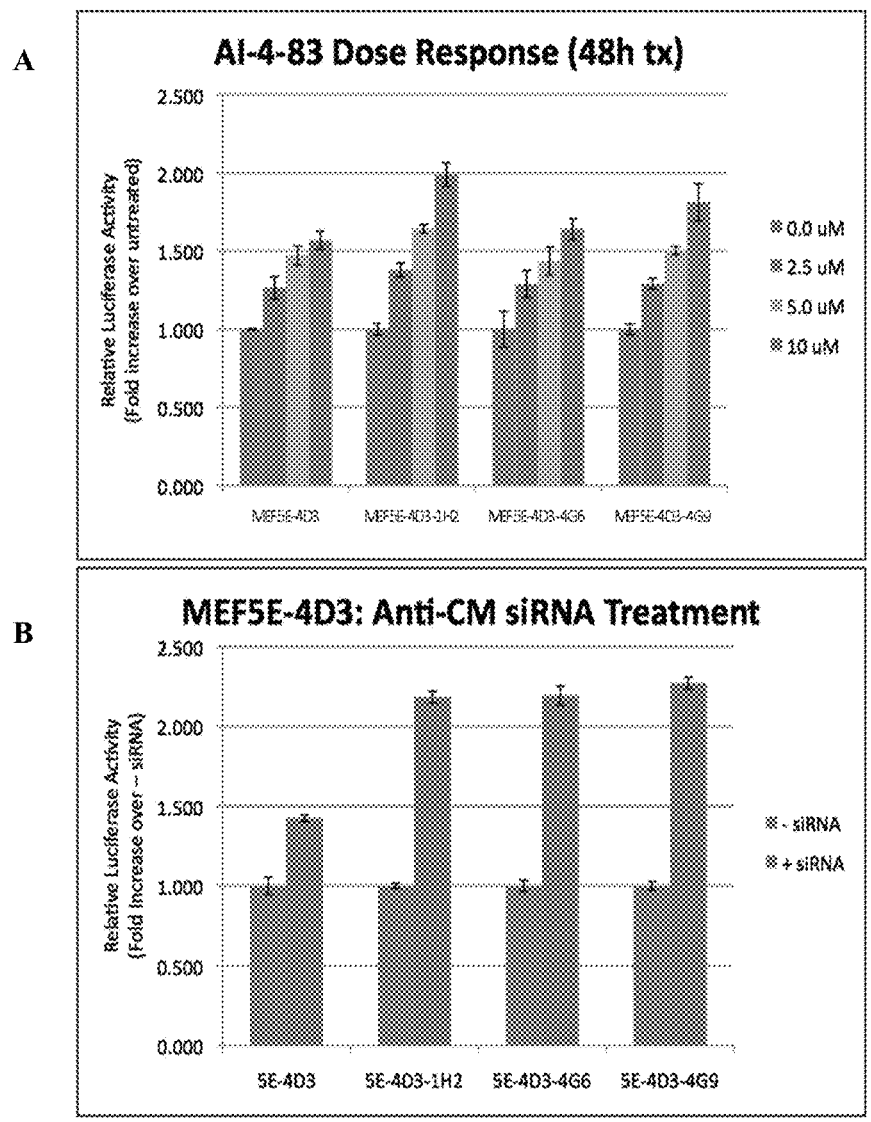
FIG. 10, comprising

A luciferase reporter assay has been developed to test the effects of inhibitors on inv(16) repression. Expression of luciferase is driven by multiple copies of a RUNX binding site using endogenous RUNX and CBFβ. CBFβ-SMMHC is expressed in these cells, resulting in repression of luciferase expression. As shown in the bottom panel of FIG. 10, siRNA knockdown of CBFβ-SMMHC results in increased luciferase activity. Similarly, treatment of cells with AI-4-83 results in a dose-dependent increase in luciferase activity which recapitulates the effect of the siRNA. These data demonstrates release of repression by the dimeric inhibitor at a RUNX regulated promoter, demonstrating the desired effect on transcription at a functional site.

Effects of Dimeric Inhibitor on Human Bone Marrow Mononuclear Cells and an Inv(16) Patient Sample.

Figure 11:
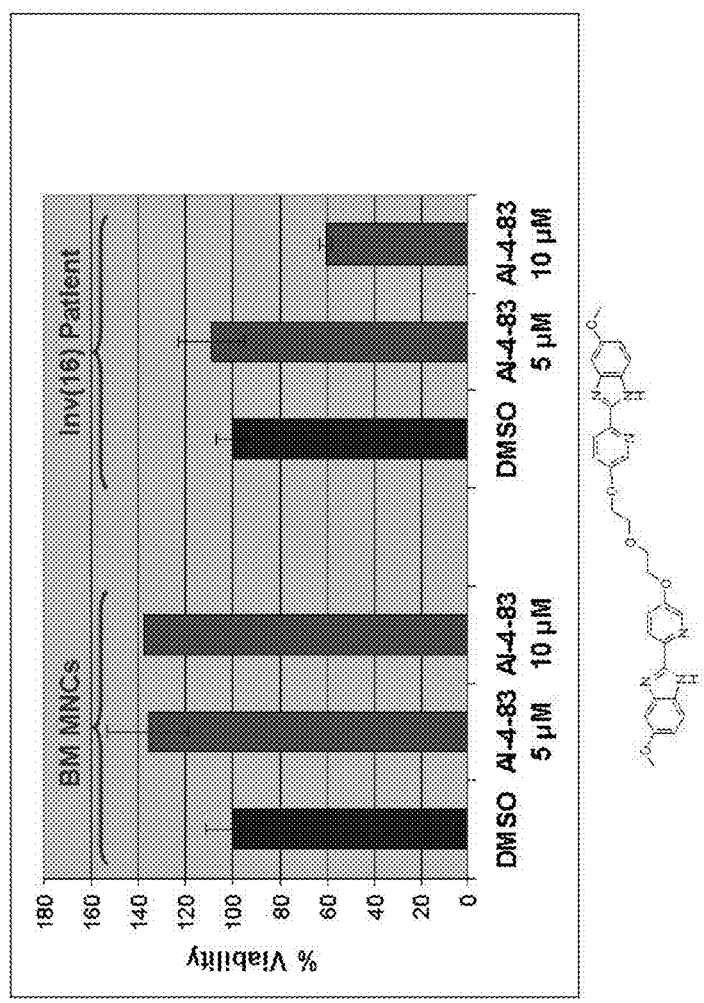
FIG. 11 depicts graphically the effect of AI-4-83 on viability on human cells. The left three bars are treatment with DMSO, AI-4-83 at 5 μM, and AI-4-83 at 10 μM and the effect on viability of human BM MNCs. The right three bars represent treatment with DMSO, AI-4-83 at 5 μM, and AI-4-83 at 10 μM and the effects on viability of cells from an inv(16) patient sample.

We have tested AI-4-83 on human bone marrow mononuclear cells (for toxicity) and on one inv(16) patient sample using an MTT assay after a 48 hour compound treatment. FIG. 11 shows that AI-4-83 has no effect on the viability of the bone marrow mononuclear cells (BM MNCs) up to 10 µM whereas there was a substantial effect on the inv(16) patient sample at the 10 µM dose. These data indicate a lack of toxicity to normal marrow mononuclear cells whereas there was a significant effect on this one inv(16) patient sample, in support of the potential for a useful therapeutic index for this class of compounds.

Effects of Dimeric Inhibitor on Mouse Leukemia Initiating Cells.

Figure 12:
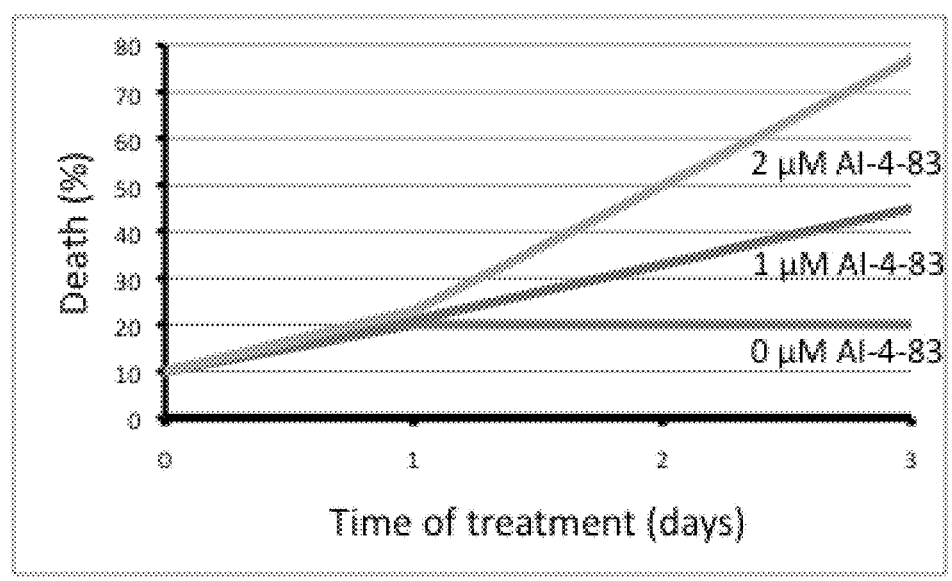
FIG. 12 depicts graphically the effect of AI-4-83 at three different doses (0.0, 1.0, and 2.0 μM) on apoptosis of inv(16) leukemia initiating cells from a mouse model.

Dr. Lucio Castilla's lab has identified a specific population of cells referred to as leukemia initiating cells using mouse models of inv(16) leukemia (Kuo, Y. H., et al., *Cbf beta-SMMHC induces distinct abnormal myeloid progenitors able to develop acute myeloid leukemia*. Cancer Cell, 2006. 9(1): p. 57-68). This population of cells retains the inv(16) but does not possess the secondary mutations associated with disease. Upon acquisition of such secondary mutations, these cells can progress to overt leukemia. These cells are also typically more resistant to traditional cytotoxic chemotherapy and therefore represent a pool of cells from which relapse can occur. We have tested AI-4-83 against this pool of cells and shown that the compound is very effective at inducing apoptosis in this population. FIG. 12 shows that a 3 day treatment with AI-4-83 at 2 µM resulted in 80% cell death while the compound had no effect on normal bone marrow mononuclear cells, i.e., the inhibitor is extremely effective at eradicating this population of cells which are a key driver of relapse.

Table 2 provides a structural and activity summary of some of the novel dimeric compounds prepared and tested herein.

TABLE 2

Activity of benzimidazole dimers

| Compound | Structure | IC$_{50}$ FRET (μM) (CBFβ-SMMHC: RD, 20 nM both) | Δ (%) |
|---|---|---|---|
| AI-4-62 (or) AI-4-83 (or) AI-10-66 | 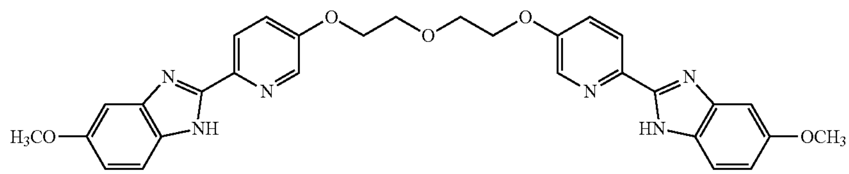 [SMILES: COc1ccc2[nH]c(-c3ccc(OCCOCCOc4ccc(-c5nc6cc(OC)ccc6[nH]5)nc4)cn3)nc2c1] | 0.59 | 45 |
| AI-4-82 | 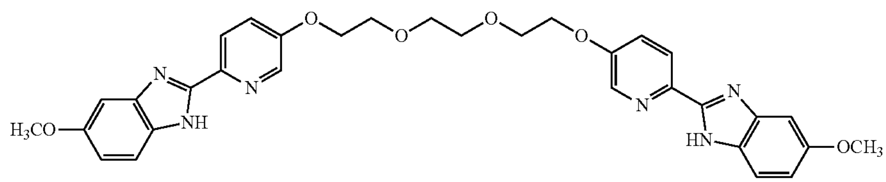 [SMILES: COc1ccc2[nH]c(-c3ccc(OCCOCCOCCOc4ccc(-c5nc6cc(OC)ccc6[nH]5)nc4)cn3)nc2c1] | 1.1 | 72 |
| AI-4-71 | 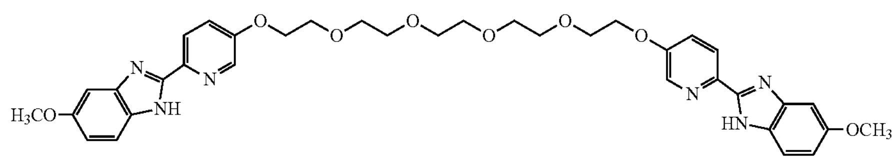 [SMILES: COc1ccc2[nH]c(-c3ccc(OCCOCCOCCOCCOCCOc4ccc(-c5nc6cc(OC)ccc6[nH]5)nc4)cn3)nc2c1] | 1.4 | 8 |
| AI-10-19 | 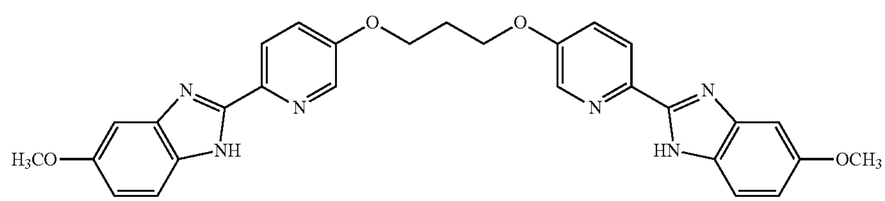 [SMILES: COc1ccc2[nH]c(-c3ccc(OCCCOc4ccc(-c5nc6cc(OC)ccc6[nH]5)nc4)cn3)nc2c1] | 1.9 | 30 |
| AI-10-42 | 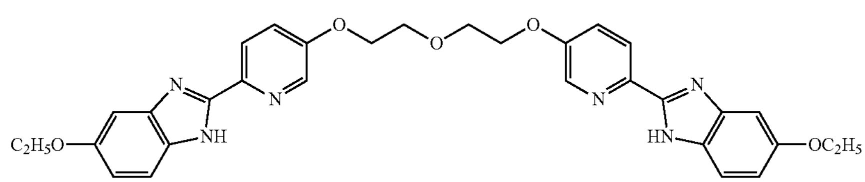 | 1.1 | 44 |
| AI-10-99 | 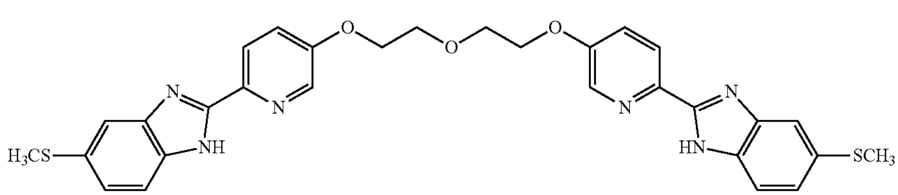 [SMILES: FC(F)(F)Oc1ccc2[nH]c(-c3ccc(OCCOCCOc4ccc(-c5nc6cc(OC(F)(F)F)ccc6[nH]5)nc4)cn3)nc2c1] | | |
| AI-10-49 | 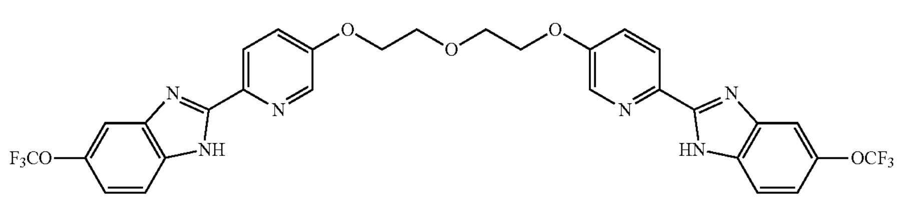 | 0.75 | 44 |
| AI-10-81 | 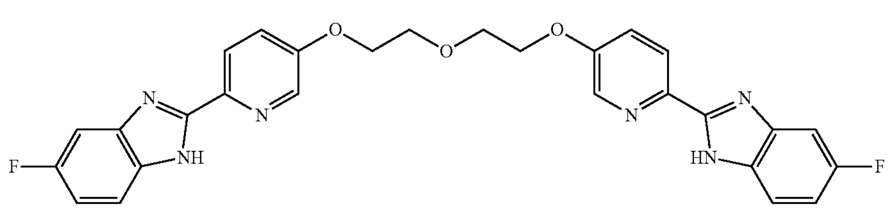 [SMILES: Fc1ccc2[nH]c(-c3ccc(OCCOCCOc4ccc(-c5nc6cc(F)ccc6[nH]5)nc4)cn3)nc2c1] | 0.7 | 31 |

TABLE 2-continued

Activity of benzimidazole dimers

| Compound | Structure | IC$_{50}$ FRET (μM) (CBFβ-SMMHC: RD, 20 nM both) | Δ (%) |
|---|---|---|---|
| AI-10-55 | 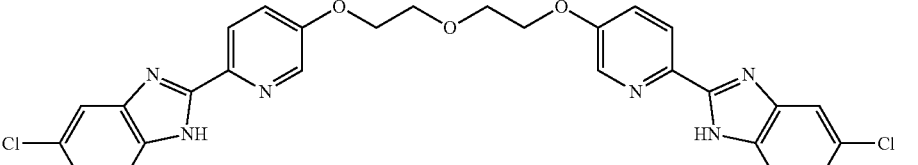 | 16 | 56 |
| AI-10-21 | 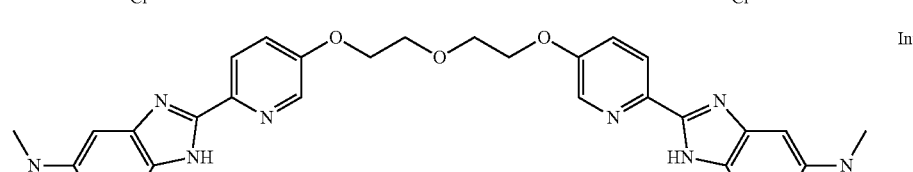 | Interference with assay | |
| AI-10-98 | 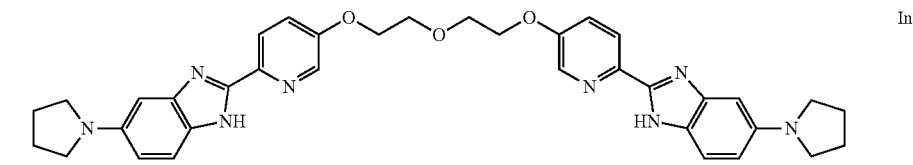 | Interference with assay | |
| AI-10-40 | 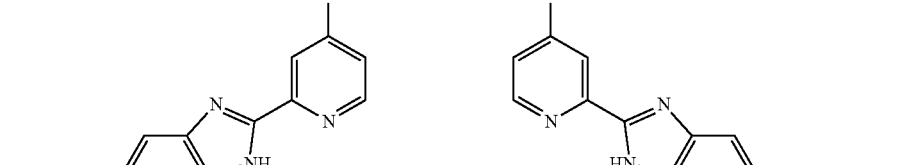 | 0.7 | 25 |

CONCLUSION

There are currently no targeted agents which act on the CBFβ-SMMHC fusion protein. Standard chemotherapy is used to treat this disease, so this would be the first targeted therapy for inv(16) leukemia.

We have demonstrated the ability to develop inhibitors with selectivity for the CBFβ-SMMHC fusion protein over the normal CBFβ protein. To our knowledge, such a high degree of selectivity has not been demonstrated previously.

The compounds we have developed target a protein-protein interaction that is important for transcriptional regulation, making it one of a small but growing class of such inhibitors.

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

BIBLIOGRAPHY

The references as cited throughout this document and below are hereby incorporated by reference herein in their entirety.

1. Adya, N., T. Stacy, et al. (1998). "The leukemic protein core binding factor beta (CBFbeta)-smooth-muscle myosin heavy chain sequesters CBFalpha2 into cytoskeletal filaments and aggregates." Mol Cell Biol 18(12): 7432-43.
2. Alcalay, M., A. Orleth, et al. (2001). "Common themes in the pathogenesis of acute myeloid leukemia." Oncogene 20(40): 5680-94.
3. Arndt, H. D. (2006). "Small molecule modulators of transcription." Angew Chem Int Ed Engl 45(28): 4552-60.
4. Backstrom, S., M. Wolf-Watz, et al. (2002). "The RUNX1 Runt Domain at 1.25 A Resolution: A Structural Switch and Specifically Bound Chloride Ions Modulate DNA Binding." J Mol Biol 322(2): 259.
5. Bartfeld, D., L. Shimon, et al. (2002). "DNA Recognition by the RUNX1 Transcription Factor Is Mediated by an Allosteric Transition in the RUNT Domain and by DNA Bending." Structure (Camb) 10(10): 1395.
6. Bazin, H., M. Preaudat, et al. (2001). "Homogeneous time-resolved fluorescence resonance energy transfer using rare earth cryptates as a tool for probing molecular interactions in biology." Spectrochim Acta A Mol Biomol Spectrosc 57(11): 2197-211.
7. Berardi, M. J., C. Sun, et al. (1999). "The Ig fold of the core binding factor alpha Runt domain is a member of a family of structurally and functionally related Ig-fold DNA-binding domains." Structure Fold Des 7(10): 1247-56.
8. Boeckx, N., V. H. van der Velden, et al. (2004). "An inv(16)(p13q22) positive acute myeloid leukaemia relapsing as acute precursor B-cell lymphoblastic leukaemia." Haematologica 89(8): ECR28.
9. Bravo, et al. (2001). "The leukemia-associated AML1 (Runx1)-CBF beta complex functions as a DNA-induced molecular clamp." Nat Struct Biol 8(4): 371-8.
10. Cai, Z., M. de Bruijn, et al. (2000). "Haploinsufficiency of AML1 affects the temporal and spatial generation of hematopoietic stem cells in the mouse embryo." Immunity 13(4): 423-31.
11. Cao, W., M. Britos-Bray, et al. (1997). "CBF beta-SMMHC, expressed in M4Eo AML, reduced CBF DNA-binding and inhibited the G1 to S cell cycle transition at the restriction point in myeloid and lymphoid cells." Oncogene 15(11): 1315-27.
12. Castilla et al., 1999, The fusion gene Cbfb-MYH11 blocks myeloid differentiation and predisposes mice to acute myelomonocytic leukaemia. Nat Genet 23(2): 144-6.
13. Castilla, L. H., P. Perrat, et al. (2004). "Identification of genes that synergize with Cbfb-MYH11 in the pathogenesis of acute myeloid leukemia." Proc Natl Acad Sci USA 101(14): 4924-9.
14. Castilla, L. H., C. Wijmenga, et al. (1996). "Failure of embryonic hematopoiesis and lethal hemorrhages in mouse embryos heterozygous for a knocked-in leukemia gene CBFB-MYH11." Cell 87(4): 687-96.
15. Castilla, L. H., C. Wijmenga, et al. (1996). "Defects of embryonic hematopoiesis and lethal hemorrhaging in mouse embryos heterozygous for a knocked-in leukemia gene CBFB-MYH11." Cell 87: 687-696.
16. Cochran, A. G. (2000). "Antagonists of protein-protein interactions." Chem Biol 7(4): R85-94.
17. Crute, B. E., A. F. Lewis, et al. (1996). "Biochemical and biophysical properties of the core-binding factor alpha2 (AML1) DNA-binding domain." J Biol Chem 271(42): 26251-60.
18. Dash, A. and D. G. Gilliland (2001). "Molecular genetics of acute myeloid leukaemia." Best Pract Res Clin Haematol 14(1): 49-64.
19. Druker, B. J. (2004). "Imatinib as a paradigm of targeted therapies." Adv Cancer Res 91: 1-30.
20. Durst, K. L., B. Lutterbach, et al. (2003). "The inv(16) fusion protein associates with corepressors via a smooth muscle myosin heavy-chain domain." Mol Cell Biol 23(2): 607-19.
21. Efeyan, A., A. Ortega-Molina, et al. (2007). "Induction of p53-dependent senescence by the MDM2 antagonist nutlin-3a in mouse cells of fibroblast origin." Cancer Res 67(15): 7350-7.
22. Farag, S. S., K. J. Archer, et al. (2006). "Pretreatment cytogenetics add to other prognostic factors predicting complete remission and long-term outcome in patients 60 years of age or older with acute myeloid leukemia: results from Cancer and Leukemia Group B 8461." Blood 108(1): 63-73.
23. Feng, B. Y. and B. K. Shoichet (2006). "A detergent-based assay for the detection of promiscuous inhibitors." Nat Protoc 1(2): 550-3.
24. Friesner, R. A., J. L. Banks, et al. (2004). "Glide: a new approach for rapid, accurate docking and scoring. 1. Method and assessment of docking accuracy." J Med Chem 47(7): 1739-49.
25. Friesner, R. A., R. B. Murphy, et al. (2006). "Extra precision glide: docking and scoring incorporating a model of hydrophobic enclosure for protein-ligand complexes." J Med Chem 49(21): 6177-96.
26. Fry, D. C. (2006). "Protein-protein interactions as targets for small molecule drug discovery." Biopolymers 84(6): 535-52.
27. Gadek, T. R. and J. B. Nicholas (2003). "Small molecule antagonists of proteins." Biochem Pharmacol 65(1): 1-8.
28. Gilliland, D. G. and M. S. Tallman (2002). "Focus on acute leukemias." Cancer Cell 1(5): 417-20.
29. Goger, M., V. Gupta, et al. (1999). "Molecular insights into PEBP2/CBF beta-SMMHC associated acute leukemia revealed from the structure of PEBP2/CBF beta." Nat Struct Biol 6(7): 620-3.
30. Goldenberg, D. P. (2003). "Computational simulation of the statistical properties of unfolded proteins." J Mol Biol 326(5): 1615-33.
31. Gorczynski, M. J., J. Grembecka, et al. (2007). "Allosteric inhibition of the protein-protein interaction between the leukemia-associated proteins Runx1 and CBFbeta." Chem Biol 14(10): 1186-97.
32. Halgren, T. A., R. B. Murphy, et al. (2004). "Glide: a new approach for rapid, accurate docking and scoring. 2. Enrichment factors in database screening." J Med Chem 47(7): 1750-9.
33. Hiebert, S. W., B. Lutterbach, et al. (2001). "Role of co-repressors in transcriptional repression mediated by the t(8;21), t(16;21), t(12;21), and inv(16) fusion proteins." Curr Opin Hematol 8(4): 197-200.
34. Ho, C. Y., B. Otterud, et al. (1996). "Linkage of a familial platelet disorder with a propensity to develop myeloid malignancies to human chromosome 21q22.1-22.2." Blood 87(12): 5218-24.
35. Huang, X., J. W. Peng, et al. (1999). "Solution structure of core binding factor beta and map of the CBF alpha binding site." Nat Struct Biol 6(7): 624-7.
36. Imbert, P. E., V. Unterreiner, et al. (2007). "Recommendations for the reduction of compound artifacts in time-resolved fluorescence resonance energy transfer assays." Assay Drug Dev Technol 5(3): 363-72.

37. Kanno, Y., T. Kanno, et al. (1998). "Cytoplasmic sequestration of the polyomavirus enhancer binding protein 2 (PEBP2)/core binding factor alpha (CBFalpha) subunit by the leukemia-related PEBP2/CBFbeta-SMMHC fusion protein inhibits PEBP2/CBF-mediated transactivation." Mol Cell Biol 18(7): 4252-61.
38. Kiessling, L. L., J. E. Gestwicki, et al. (2006). "Synthetic multivalent ligands as probes of signal transduction." Angewandte Chemie-International Edition 45(15): 2348-2368.
39. Kottaridis, P. D., R. E. Gale, et al. (2002). "Studies of FLT3 mutations in paired presentation and relapse samples from patients with acute myeloid leukemia: implications for the role of FLT3 mutations in leukemogenesis, minimal residual disease detection, and possible therapy with FLT3 inhibitors." Blood 100(7): 2393-8.
40. Kuo, Y. H., S. F. Landrette, et al. (2006). "Cbf beta-SMMHC induces distinct abnormal myeloid progenitors able to develop acute myeloid leukemia." Cancer Cell 9(1): 57-68.
41. Lacaud, G., V. Kouskoff, et al. (2004). "Haploinsufficiency of Runx1 results in the acceleration of mesodermal development and hemangioblast specification upon in vitro differentiation of ES cells." Blood 103(3): 886-9.
42. Li, Z., J. Yan, et al. (2003). "Energetic contribution of residues in the Runx1 Runt domain to DNA binding." J Biol Chem 278: 33088-33096.
43. Liu, P., S. A. Tarle, et al. (1993). "Fusion between transcription factor CBF beta/PEBP2 beta and a myosin heavy chain in acute myeloid leukemia." Science 261 (5124): 1041-4.
44. Liu, P. P., C. Wijmenga, et al. (1996). "Identification of the chimeric protein product of the CBFB-MYH11 fusion gene in inv(16) leukemia cells." Genes Chromosomes Cancer 16(2): 77-87.
45. Look, A. T. (1997). "Oncogenic transcription factors in the human acute leukemias." Science 278(5340): 1059-64.
46. Lu, J., M. Maruyama, et al. (1995). "Subcellular localization of the alpha and beta subunits of the acute myeloid leukemia-linked transcription factor PEBP2/CBF." Mol Cell Biol 15(3): 1651-61.
47. Lukasik, S. M., L. Zhang, et al. (2002). "Altered affinity of CBFbeta-SMMHC for Runx1 explains its role in leukemogenesis." Nat Struct Biol 9(9): 674-9.
48. Lutterbach, B., Y. Hou, et al. (1999). "The inv(16) encodes an acute myeloid leukemia 1 transcriptional corepressor." Proc Natl Acad Sci USA 96(22): 12822-7.
49. Lydon, N. B. and B. J. Druker (2004). "Lessons learned from the development of imatinib." Leuk Res 28 Suppl 1: S29-38.
50. Mammen, M., S. K. Choi, et al. (1998). "Polyvalent interactions in biological systems: Implications for design and use of multivalent ligands and inhibitors." Angewandte Chemie-International Edition 37(20): 2755-2794.
51. Markus, J., M. T. Garin, et al. (2007). "Methylation-independent silencing of the tumor suppressor INK4b (p15) by CBFbeta-SMMHC in acute myelogenous leukemia with inv(16)." Cancer Res 67(3): 992-1000.
52. Mosmann, T. (1983). "Rapid colorimetric assay for cellular growth and survival: application to proliferation and cytotoxicity assays." J Immunol Methods 65(1-2): 55-63.
53. Mulder, A., T. Auletta, et al. (2004). "Divalent binding of a bis(adamantyl)-functionalized calix[4]arene to beta-cyclodextrin-based hosts: An experimental and theoretical study on multivalent binding in solution and at self-assembled monolayers." Journal of the American Chemical Society 126(21): 6627-6636.
54. Nagata, T., V. Gupta, et al. (1999). "Immunoglobulin motif DNA recognition and heterodimerization of the PEBP2/CBF Runt domain." Nat Struct Biol 6(7): 615-9.
55. Nakano, Y., H. Kiyoi, et al. (1999). "Molecular evolution of acute myeloid leukaemia in relapse: unstable N-ras and FLT3 genes compared with p53 gene." Br J Haematol 104(4): 659-64.
56. North, T. E., M. F. de Bruijn, et al. (2002). "Runx1 expression marks long-term repopulating hematopoietic stem cells in the midgestation mouse embryo." Immunity 16(5): 661-72.
57. Okuda, T., J. van Deursen, et al. (1996). "AML1, the target of multiple chromosomal translocations in human leukemia, is essential for normal fetal liver hematopoiesis." Cell 84(2): 321-30.
58. Okuda, T., J. van Deursen, et al. (1996). "AML1, the target of multiple chromosomal translocations in human leukemia, is essential for normal fetal liver hematopoiesis." Cell 84: 321-330.
59. Osato, M., M. Yanagida, et al. (2001). "Point mutations of the RUNx1/AML1 gene in sporadic and familial myeloid leukemias." Int J Hematol 74(3): 245-51.
60. Pellecchia, M., D. S. Sem, et al. (2002). "NMR in drug discovery." Nat Rev Drug Discov 1(3): 211-9.
61. Perez-Alvarado, G. C., A. Munnerlyn, et al. (2000). "Identification of the regions involved in DNA binding by the mouse PEBP2alpha protein." FEBS Lett 470(2): 125-30.
62. Pulsoni, A., S. Iacobelli, et al. (2008). "M4 acute myeloid leukemia: the role of eosinophilia and cytogenetics in treatment response and survival. The GIMEMA experience." Haematologica 93(7): 1025-32.
63. Ravandi, F., A. K. Burnett, et al. (2007). "Progress in the treatment of acute myeloid leukemia." Cancer 110(9): 1900-10.
64. Reilly, J. T. (2005). "Pathogenesis of acute myeloid leukaemia and inv(16)(p13;q22): a paradigm for understanding leukaemogenesis?" Br J Haematol 128(1): 18-34.
65. Salvatella, X. and E. Giralt (2003). "NMR-based methods and strategies for drug discovery." Chem Soc Rev 32(6): 365-72.
66. Sasaki, K., H. Yagi, et al. (1996). "Absence of fetal liver hematopoiesis in mice deficient in transcriptional coactivator core binding factor beta." Proc Natl Acad Sci USA 93(22): 12359-63.
67. Sasaki, K., H. Yagi, et al. (1996). "Absence of fetal liver hematopoiesis in transcriptional co-activator, core binding factor b (Cbfb) deficient mice." Proc. Natl. Acad. Sci. USA 93: 12359-12363.
68. Seidler et al. (2003). "Identification and prediction of promiscuous aggregating inhibitors among known drugs." J Med Chem 46(21): 4477-86.
69. Shangary, S., D. Qin, et al. (2008). "Temporal activation of p53 by a specific MDM2 inhibitor is selectively toxic to tumors and leads to complete tumor growth inhibition." Proc Natl Acad Sci USA 105(10): 3933-8.
70. Sharma, S. V. and J. Settleman (2007). "Oncogene addiction: setting the stage for molecularly targeted cancer therapy." Genes Dev 21(24): 3214-31.
71. Shigesada, K., B. van de Sluis, et al. (2004). "Mechanism of leukemogenesis by the inv(16) chimeric gene CBFB/PEBP2B-MHY11." Oncogene 23(24): 4297-307.

72. Shih et al. (2008). "Cooperating mutations of receptor tyrosine kinases and Ras genes in childhood core-binding factor acute myeloid leukemia and a comparative analysis on paired diagnosis and relapse samples." Leukemia 22(2): 303-7.
73. Song et al. (1999). "Haploinsufficiency of CBFA2 causes familial thrombocytopenia with propensity to develop acute myelogenous leukaemia." Nat Genet 23(2): 166-75.
74. Tahirov et al. 2001, Structural analyses of DNA recognition by the AML1/Runx-1 Runt domain and its allosteric control by CBFbeta. Cell 104(5): 755-67.
75. Talebian, L., Z. Li, et al. (2007). "T-lymphoid, megakaryocyte, and granulocyte development are sensitive to decreases in CBFbeta dosage." Blood 109(1): 11-21.
76. Tang, Y. Y., B. E. Crute, et al. (2000). "Biophysical characterization of interactions between the core binding factor alpha and beta subunits and DNA." FEBS Lett 470(2): 167-72.
77. Tang, Y. Y., J. Shi, et al. (2000). "Energetic and functional contribution of residues in the core binding factor beta (CBFbeta) subunit to heterodimerization with CBFalpha." J Biol Chem 275(50): 39579-88.
78. Toogood, P. L. (2002). "Inhibition of protein-protein association by small molecules: approaches and progress." J Med Chem 45(8): 1543-58.
79. Tovar, C., J. Rosinski, et al. (2006). "Small-molecule MDM2 antagonists reveal aberrant p53 signaling in cancer: implications for therapy." Proc Natl Acad Sci USA 103(6): 1888-93.
80. Vassilev, L. T., B. T. Vu, et al. (2004). "In vivo activation of the p53 pathway by small-molecule antagonists of MDM2." Science 303(5659): 844-8.
81. Veselovsky, A. V., Y. D. Ivanov, et al. (2002). "Protein-protein interactions: mechanisms and modification by drugs." J Mol Recognit 15(6): 405-22.
82. Wang, Q., T. Stacy, et al. (1996). "Disruption of the Cbfa2 gene causes necrosis and hemorrhaging in the central nervous system and blocks definitive hematopoiesis." Proc Natl Acad Sci USA 93(8): 3444-9.
83. Wang, Q., T. Stacy, et al. (1996). "Disruption of the Cbfa2 gene causes necrosis and hemorrhaging in the central nervous system and blocks definitive hematopoiesis." Proc. Natl. Acad. Sci. USA 93: 3444-3449.
84. Wang, Q., T. Stacy, et al. (1996). "The CBFbeta subunit is essential for CBFalpha2 (AML1) function in vivo." Cell 87(4): 697-708.
85. Wang, Q., T. Stacy, et al. (1996). "The CBFb subunit is essential for CBFa2 (AML1) function in vivo." Cell 87: 697-708.
86. Weinstein, I. B. and A. Joe (2008). "Oncogene addiction." Cancer Res 68(9): 3077-80; discussion 3080.
87. Xu, M., D. Li, et al. (2007). "Leukemogenic AML1-ETO fusion protein increases carcinogen-DNA adduct formation with upregulated expression of cytochrome P450-1A1 gene." Exp Hematol 35(8): 1249-55.
88. Yan, J., Y. Liu, et al. (2004). "CBFbeta allosterically regulates the Runx1 Runt domain via a dynamic conformational equilibrium." Nat Struct Mol Biol 11(9): 901-6.
89. Yanagisawa, K., T. Horiuchi, et al. (1991). "Establishment and characterization of a new human leukemia cell line derived from M4E0." Blood 78(2): 451-7.
90. Zhang, L., Z. Li, et al. (2003). "Mutagenesis of the Runt domain defines two energetic hotspots for heterodimerization with the core binding factor beta subunit." J Biol Chem 278: 33097-33104.

What is claimed is:

1. A compound selected from the group consisting of:

LD-1-138

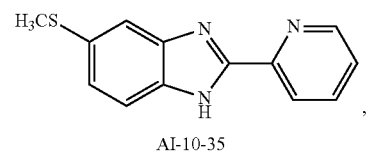

AI-10-35

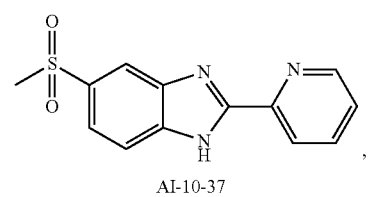

AI-10-37

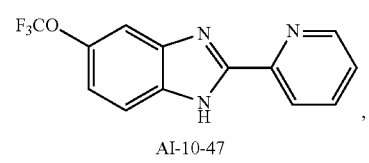

AI-10-47

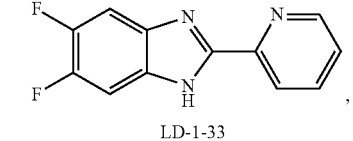

LD-1-33

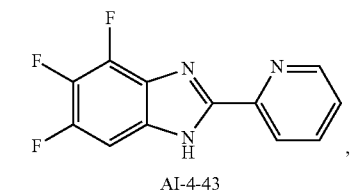

AI-4-43

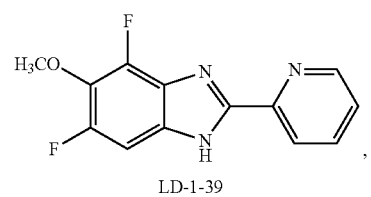

LD-1-39

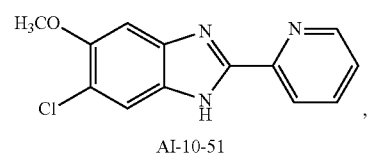

AI-10-51

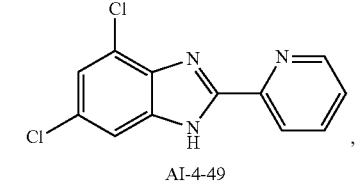

AI-4-49

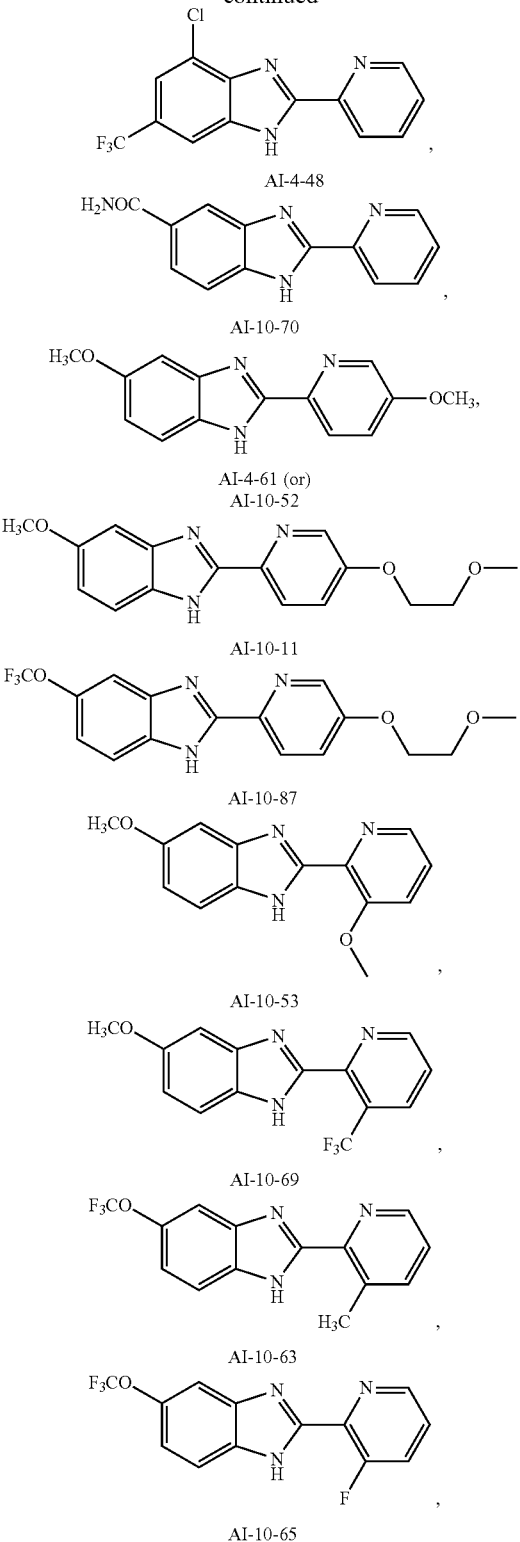
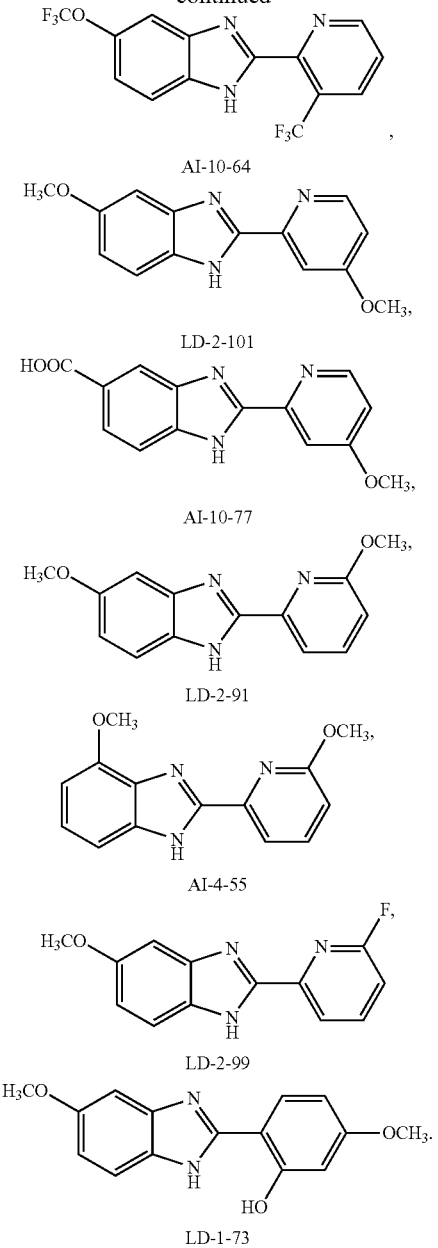

2. A method of inhibiting inv(16) leukemia cell proliferation, said method comprising contacting an inv(16) leukemia cell with a pharmaceutical composition comprising an effective amount of a compound of claim 1.

3. A method of treating inv(16) leukemia is a subject in need thereof, said method comprising administering to said subject a pharmaceutical composition comprising a pharmaceutically acceptable-carrier and a therapeutically effective amount of a compound of claim 1.

* * * * *